US 6,627,397 B1

United States Patent
Nakamura et al.

(10) Patent No.: US 6,627,397 B1
(45) Date of Patent: Sep. 30, 2003

(54) MEASURING CHIP FOR SURFACE PLASMON RESONANCE BIOSENSOR AND METHOD FOR PRODUCING THE SAME

(75) Inventors: Runa Nakamura, Tokyo-To (JP); Hiroyuki Nakamura, Tokyo-To (JP); Ryohei Nagata, Tokyo-To (JP); Isao Karube, Kawasaki (JP); Hitoshi Muguruma, Kochi-Ken (JP)

(73) Assignees: DAI Nippon Printing Co., Ltd., Tokyo-To (JP); Isao Karube, Kawasaki (JP)

( * ) Notice: Subject to any disclaimer, the term of this patent is extended or adjusted under 35 U.S.C. 154(b) by 0 days.

(21) Appl. No.: 09/274,321

(22) Filed: Mar. 23, 1999

(30) Foreign Application Priority Data

Mar. 24, 1998 (JP) .............................. 10-076144
May 18, 1998 (JP) .............................. 10-134780
Jan. 20, 1999 (JP) .............................. 11-012233

(51) Int. Cl.[7] .............................. C12Q 1/68; G01N 1/00; G01N 15/00; B01J 8/00; C07H 21/00
(52) U.S. Cl. .............................. 435/6; 422/50; 422/55; 422/57; 422/68.1; 422/69; 422/129; 436/501; 536/22.1; 536/24.3; 536/25.3
(58) Field of Search .............................. 422/50, 55, 57, 422/68.1, 69, 82.05, 82.06, 129; 435/6; 436/501; 536/22.1, 23.1, 24.3, 25.3

(56) References Cited

U.S. PATENT DOCUMENTS

| 5,341,215 A | * | 8/1994 | Seher .......................... 356/445 |
| 5,494,829 A | * | 2/1996 | Sandstrom et al. .......... 436/518 |
| 5,876,753 A | * | 3/1999 | Timmons et al. ............ 427/488 |
| 5,976,466 A | * | 11/1999 | Ratner et al. ............. 422/82.11 |

FOREIGN PATENT DOCUMENTS

JP  9-264843  10/1997

OTHER PUBLICATIONS

R. Nakamura, et al., Analytical Chemistry, vol. 69, No. 22, pps. 4649–4652, "A Plasma–Polymerized Film for Surface Plasmon Resonance Immunosensing," Nov. 15, 1997.
H. Yasuda, Academic Press Inc., pp. 77 & 111, "Plasma Polymerization," 1985.
Patent Abstracts of Japan, vol. 015, No. 398 (C–0874), Oct. 9, 1991, JP 03 164195, Jul. 16, 1991.

* cited by examiner

Primary Examiner—Ardin H. Marschel
(74) Attorney, Agent, or Firm—Oblon, Spivak, McClelland, Maier & Neustadt, P.C.

(57) ABSTRACT

An objective of the present invention is to provide a measuring chip for a surface plasmon resonance sensor that can detect a small amount of target substances in high sensitivity. The present invention provides a measuring chip for a surface plasmon resonance sensor comprising a metal layer, one or more plasma polymerization layers formed on said metal layer, and a biologically active substance immobilized on the surface of said plasma polymerization layer.

16 Claims, 15 Drawing Sheets

(a)

(b)

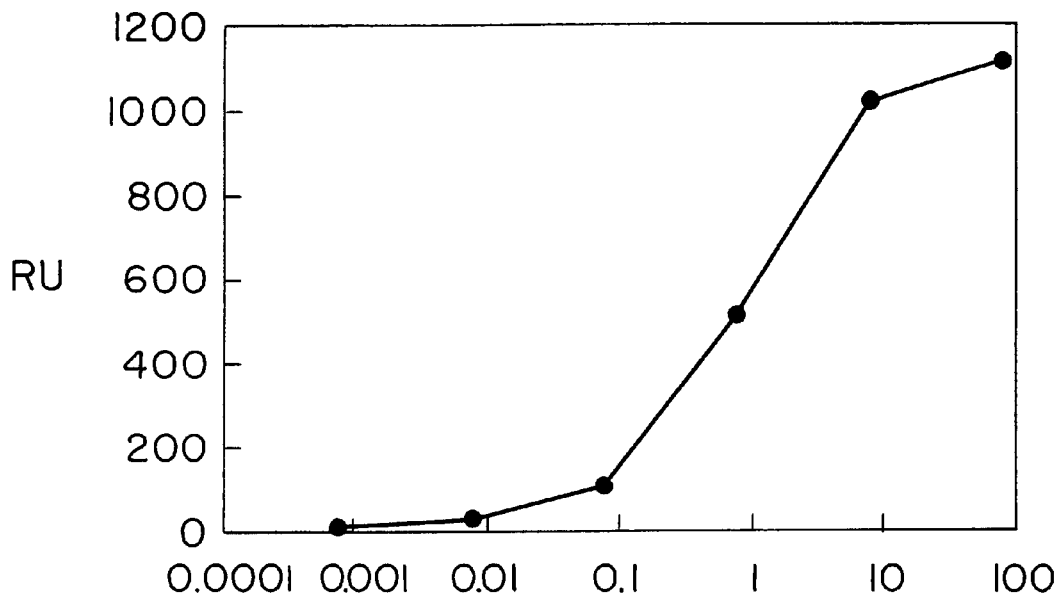
F I G. 8
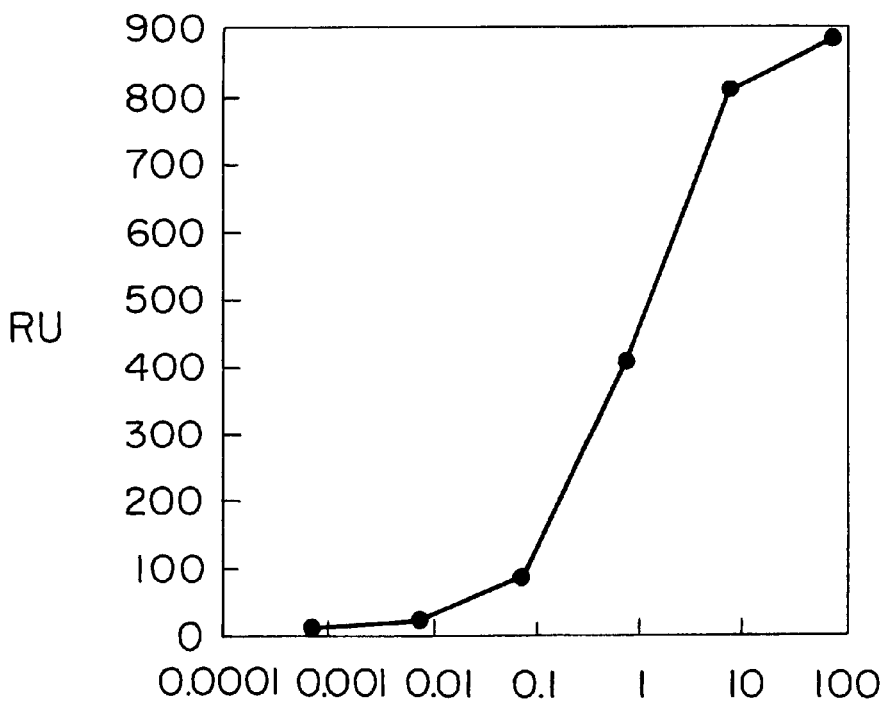
F I G. 9

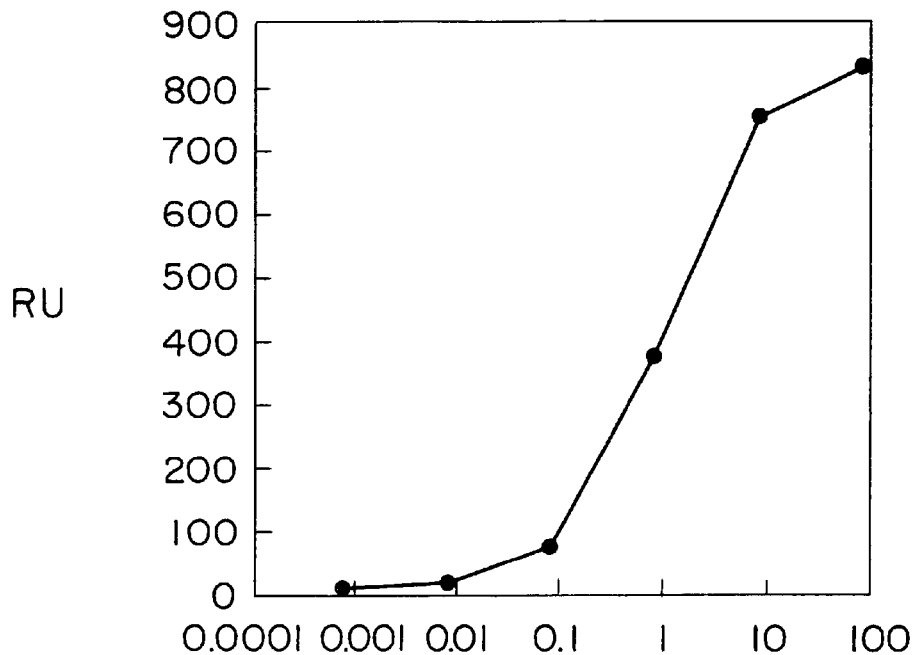
F I G. 10
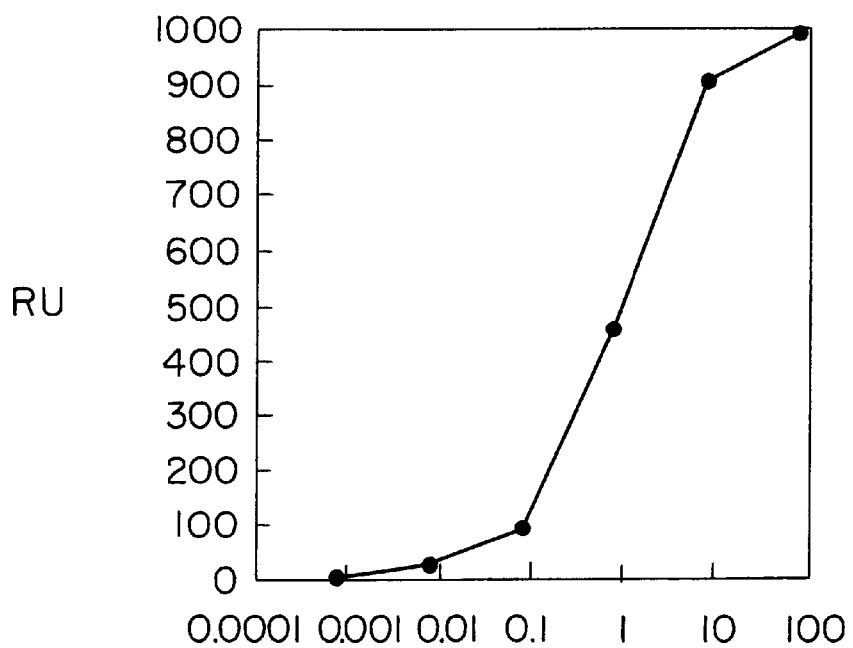
F I G. 11

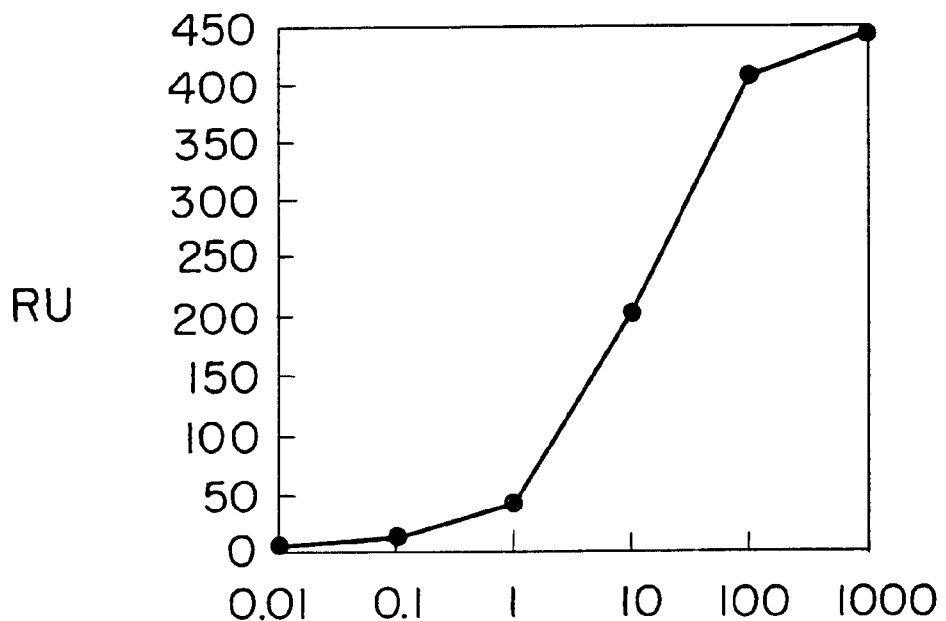
F I G. 14
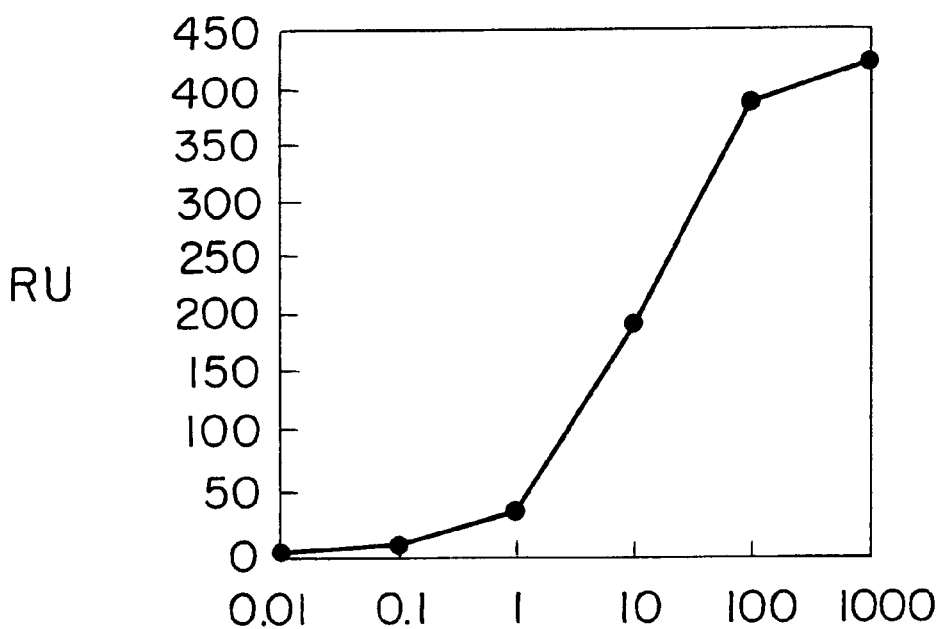
F I G. 15

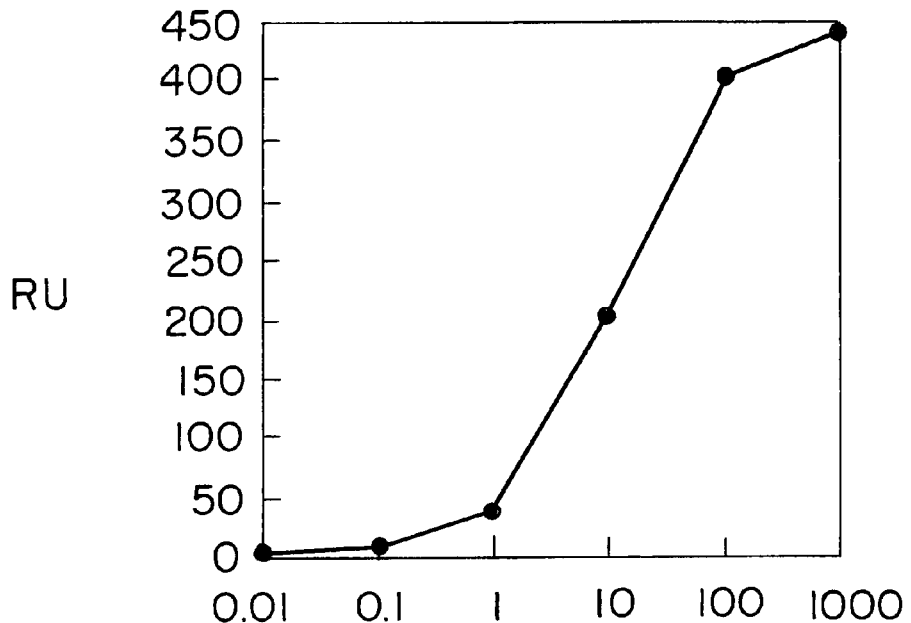
F I G. 16
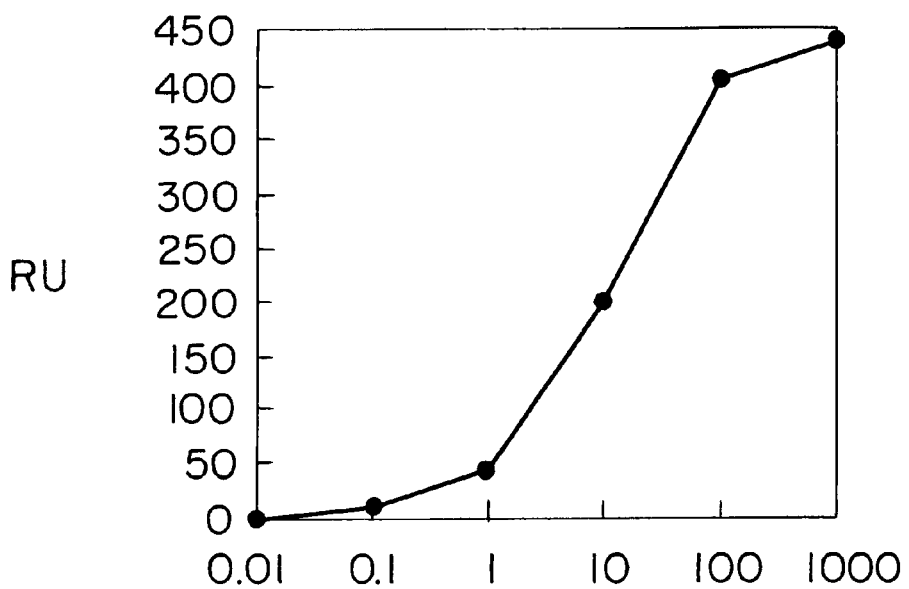
F I G. 17

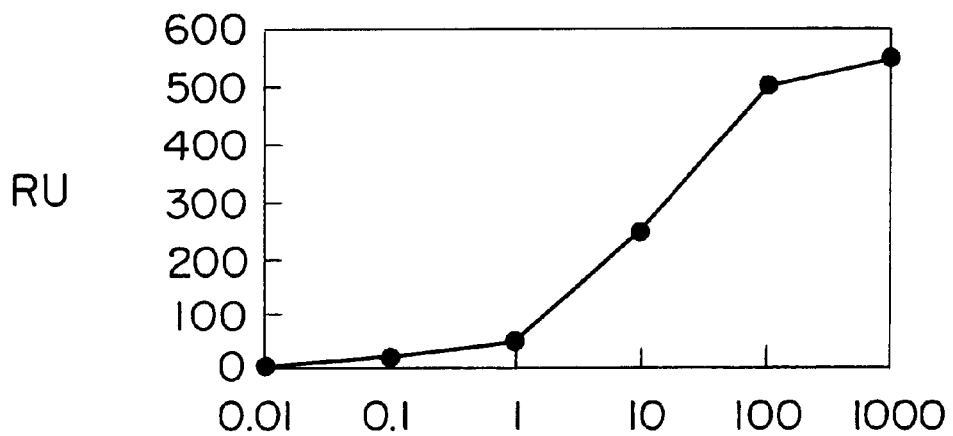
F I G. 22
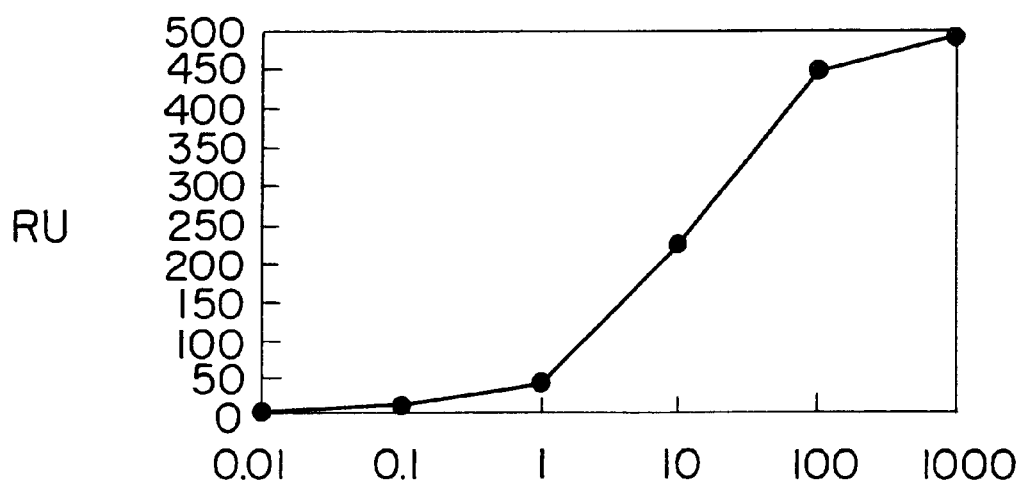
F I G. 23

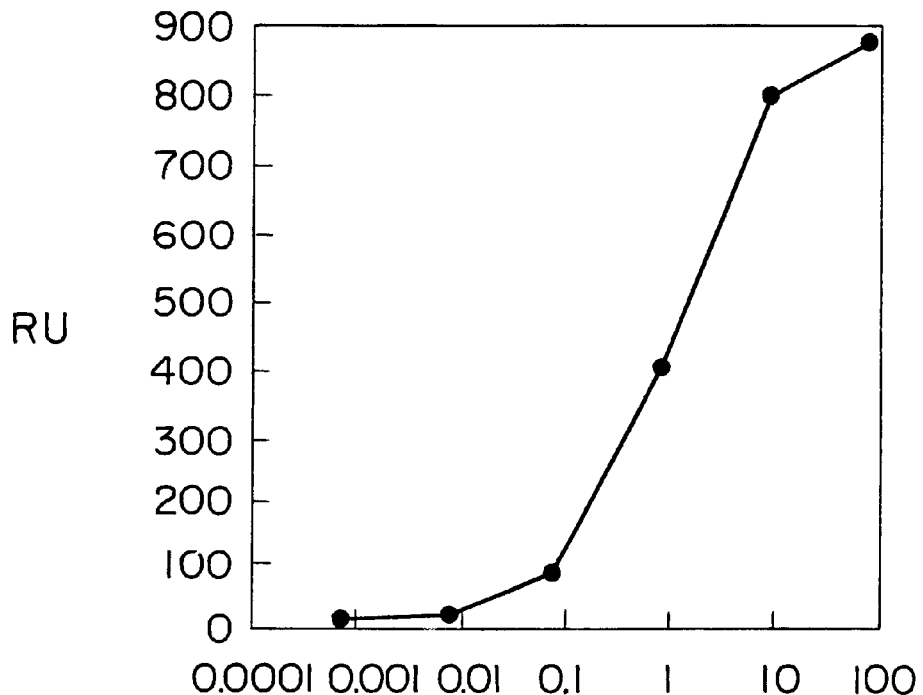
F I G. 24
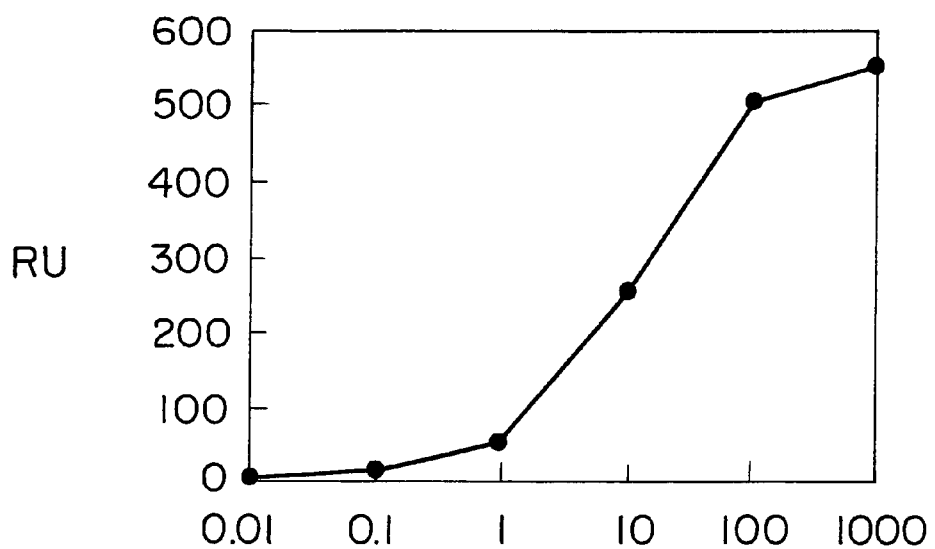
F I G. 25

MEASURING CHIP FOR SURFACE PLASMON RESONANCE BIOSENSOR AND METHOD FOR PRODUCING THE SAME

BACKGROUND OF THE INVENTION

1. Field of the Invention

The present invention relates to a surface plasmon resonance biosensor, specifically, a measuring chip for the same and a method for producing the measurement chip.

2. Background Art

A number of methods using immunological reactions are used in clinical tests for detecting target substances. Conventional methods are known to be intricate and require labeling substances. Thus, immunological sensors using a surface plasmon resonance biosensor (SPR) is being used, in which no labeling substance is required and a ligand can be detected with high sensitivity. This surface plasmon resonance biosensor is based on the phenomenon that the intensity of a monochromatic light reflected from the interface between an optically transparent substance such as glass and a metal thin-film layer is dependent on the refractive index of a sample placed on the reflecting side of the metal. Accordingly, a sample can be analyzed by measuring the intensity of the reflected monochromatic light.

An optical part of a measuring cell for this surface plasmon resonance (surface plasmon resonance biosensor) has a structure shown in FIG. 2. Namely, porous material 5 is formed on metal thin-film 2 formed on glass substrate 1, and physiologically active substance 4, such as an enzyme or antibody, is retained or immobilized on the surface or inside of porous material 5. Examples of porous material 5 to be used include weaved, knitted or non-woven cloths made of synthetic fibers, natural fibers, inorganic fibers or the like, and porous inorganic or organic materials (see Japanese Patent Laid-open No. 164195/1991). Furthermore, carboxymethyl dextran is used as a porous material in a commercial product (BIAcore 2000, Pharmacia Biosensor).

However, physiologically active substance 4 just exists on the surface of porous material 5 and interacts with target substances.

LB (Langmuir-Blodgett) method is occasionally used to immobilize physiologically active substance 4 on metal thin-film 2 (see Japanese Patent Laid-open No. 288672/1993). However, this method has a disadvantage in that LB membrane binds poorly to a metal thin-film and peels off together with the physiologically active substance.

Furthermore, Japanese Patent Laid-open No. 264843/1997 discloses measuring cells for a surface plasmon resonance biosensor.

SUMMARY OF THE INVENTION

The present inventors have now found that sensitivity of a measuring chip for a surface plasmon resonance sensor is extremely improved when only a small amount of a physiologically active substance is immobilized on a specific plasma polymerization layer.

An objective of the present invention is to provide a measuring chip for a surface plasmon resonance sensor that can detect a small amount of target substances in high sensitivity.

Another objective of the present invention is to provide a measuring cell for a surface plasmon resonance sensor that can detect a small amount of target substances in high sensitivity.

Further objective of the present invention is to provide a method for producing said measuring chip.

The present invention provides a measuring chip for a surface plasmon resonance sensor comprising a metal layer and one or more plasma polymerization layers formed on said metal layer.

The present invention also provides a measuring chip for a surface plasmon resonance sensor comprising a metal layer, one or more plasma polymerization layers formed on said metal layer, and a biologically active substance immobilized on the surface of said plasma polymerization layer.

The present invention also provides a measuring cell for a surface plasmon resonance sensor comprising said measuring chip.

The present invention also provides a method for producing a measuring chip for a surface plasmon resonance sensor comprising the steps of forming a metal layer on an optically transparent substrate, forming one or more plasma polymerization layers on said metal layer, and then immobilizing a biologically active substance on the surface of said plasma polymerization layer.

BRIEF DESCRIPTION OF THE DRAWINGS

FIG. 8 shows the relationship between the concentration of the complementary DNA and RU in Example 1.

FIG. 9 shows the relationship between the concentration of the complementary DNA and RU in Example 2.

FIG. 10 shows the relationship between the concentration of the complementary DNA and RU in Example 3.

FIG. 11 shows the relationship between the concentration of the complementary DNA and RU in Example 4.

FIG. 14 shows the relationship between the concentration of the sugar and RU in Example 7.

FIG. 15 shows the relationship between the concentration of the BSA antigen and RU in Example 8.

FIG. 16 shows the relationship between the concentration of the BSA antigen and RU in Example 9.

FIG. 17 shows the relationship between the concentration of the BSA antigen and RU in Example 10.

FIG. 22 shows the relationship between the concentration of the HSA antigen and RU in Example 15.

FIG. 23 shows the relationship between the concentration of the HSA antigen and RU in Example 16.

FIG. 24 shows the relationship between the concentration of the complementary DNA and RU in Example 17.

FIG. 25 shows the relationship between the concentration of the HSA antigen and RU in Example 18.

DETAILED DESCRIPTION OF THE INVENTION

Figure 1:
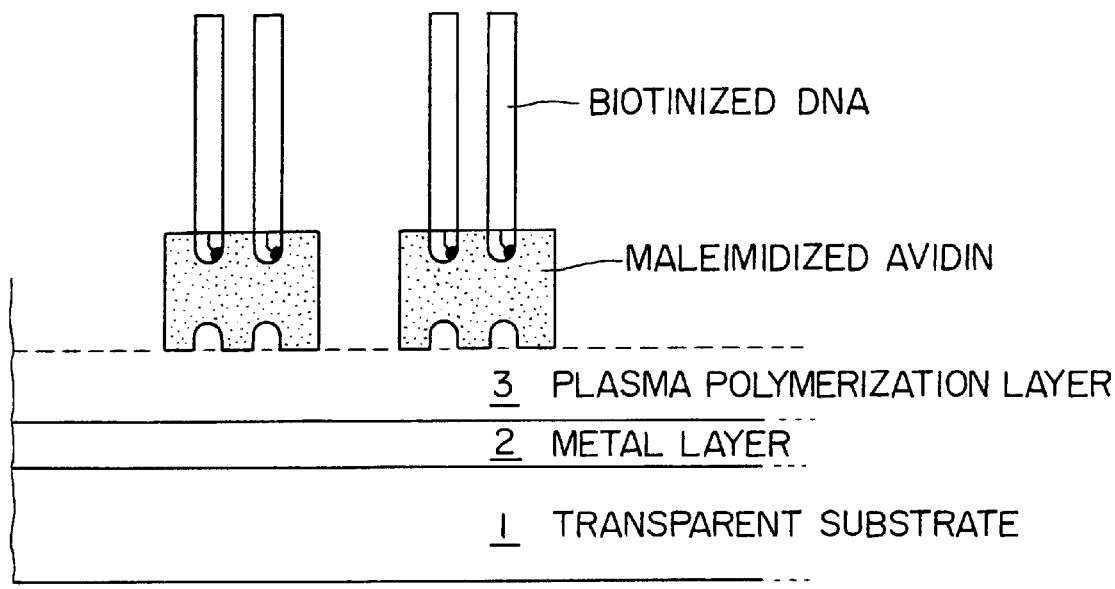
FIG. 1 is a schematic sectional view of one embodiment of the measuring chip for a surface plasmon resonance sensor according to the present invention.
Figure 2:
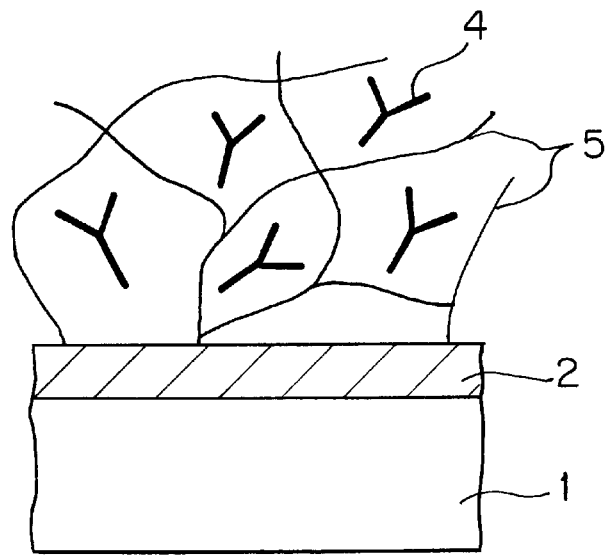
FIG. 2 is a schematic sectional view of an optical part of measuring chip for a conventional surface plasmon resonance biosensor. 1: Transparent substrate; 2: Metalthin-film; 3: Plasma polymerization layer; 4: Physiologically active substance; 5: Porous material.

The measuring chip for a surface plasmon resonance sensor ("measuring chip") may have optically transparent substrate (transparent substrate) 1, metal thin-film 2 formed on transparent substrate 1, plasma polymerization layer 3 formed on metal thin-film 2, and physiologically active substance 4 immobilized on the surface of plasma polymerization layer 3 as shown in FIG. 1.

Transparent substrate 1 can be any substrate customarily used in a measuring chip for a surface plasmon resonance sensor. Generally, substrates made of materials that are transparent to a laser beam such as glass can be used. The thickness of the substrate can be about 0.1 to 5 mm.

Metal thin-film 2 is not particularly restricted, provided it can induce surface plasmon resonance. Examples of the metal to be used for metal thin-film 2 include gold, silver and platinum. They can be used alone or in combination. Furthermore, for better adhesion to transparent substrate 1, an auxiliary layer made of chrome or the like may be set between transparent substrate 1 and the layer made of gold, silver or the like.

The thickness of metal thin-film 2 is preferably 100 to 2000 angstroms, most preferably 100 to 500 angstroms. If the thickness exceeds 3,000 angstroms, surface plasmon phenomena of the medium cannot be sufficiently detected. Furthermore, when an auxiliary layer made of chrome or the like is formed, the thickness of the auxiliary layer is preferably 30 to 50 angstroms.

Plasma polymerization layer 3 can be formed by plasma polymerization of a monomer material for three-dimensional cross-linking. A monomer material to be used in the present invention can be any material that can immobilize a physiologically active substance by plasma polymerization.

Examples of a monomer material for a plasma polymerization layer include compounds of formula (I):

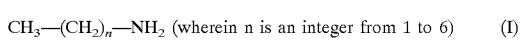
$CH_3-(CH_2)_n-NH_2$ (wherein n is an integer from 1 to 6)   (I)

and compounds of formula (II):

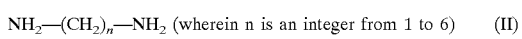
$NH_2-(CH_2)_n-NH_2$ (wherein n is an integer from 1 to 6)   (II)

and compounds which comprise carbon (C), hydrogen (H) and nitrogen (N) and have double bonds or triple bonds, such as acetonitrile, vinylamine and pyridine.

Furthermore, when a cross-linking reagent or a condensation reagent is used as a linking layer, a compound further containing sulfur (S), oxygen (O) or silicon (Si) can be used as a monomer material. Generally, a compound appropriately containing any two or more elements selected from carbon (C), hydrogen (H), nitrogen (N), sulfur (S), oxygen (O) and silicon (Si) can be used. In addition, a halogen gas or a rare gas can be used as a monomer material.

In the present invention, a compound containing nitrogen can be used as a monomer material. Examples of the compound containing nitrogen include nitrogen $N_2$; ammonium; hydrazine; pyridine; compounds of formulae (I) and (II) such as ethylenediamine $NH_2(CH_2)_2NH_2$, hexamethylenediamine $NH_2(CH_2)_6NH_2$, n-propylamine $CH_3(CH_2)_2NH_2$ and monoethylamine $CH_3(CH_2)NH$; compounds of formula $(CH_3)_3(CH_2)_nN$ (n=0 to 17) such as triethylamine $(C_2H_5)_3N$; compounds of formula $(CH_3)_2(CH_2)_nNH$ (n=0 to 17) such as diethylamine $(C_2H_5)_2NH$; compounds of formula $CH_2=CH(CH_2)_nNH_2$ (n=O to 17) such as allylamine $CH_2=CHCH_2NH_2$; compounds of formula $CH_3(CH_2)_nCN$ (n=0 to 17) such as acetonitrile $CH_3CN$; compounds of formula $CH_3 (CH_2)_nCN$; propargylamine $CHCCH_2NH_2$; compounds of formula $CHC (CH_2)_nNH_2$; acrylamide; aniline; acrylonitrile; 1,2,4-triazole; and 5-amino-1H-tetrazole.

Further examples of the compound containing nitrogen include the following:

$RaNRb_2$:
Ra is H or $CH_3(CH_2)_n$(n=0 to 17),
and includes a group having a double bond or a triple bond or both in the chain, and further a branched or cyclized group, and
Rb is H or $CH_3(CH_2)_n$(n=0 to 17),
and includes a group having a double bond or a triple bond or both in the chain, and further a branched or cyclized group;

$RaNRc$:
Rc is H or $CH_3(CH_2)_nCH$ (n=0 to 17), or $CH_2$,
and includes a group having a double bond or a triple bond or both in the chain, and further a branched or cyclized group;

RdN:
Rd is $CH_3(CH_2)_nC$ (n=0 to 17) or CH, and includes a group having a double bond or a triple bond or both in the chain, and further a branched or cyclized group;

ReNRfNRg$_2$:
Re is H or $CH_3(CH_2)_n$ (n=0 to 17), and includes a group having a double bond or a triple bond or both in the chain, and further a branched or cyclized group,
Rf is $(CH_2)_n$ (n=0 to 17), and includes a group having a double bond or a triple bond or both in the chain, and further a branched or cyclized group,
Rg is H or $CH_3(CH_2)_n$ (n=0 to 17), and includes a group having a double bond or a triple bond or both in the chain, and further a branched or cyclized group;

RhNRiNRj
Rh is H or $CH_3(CH_2)_n$ (n=0 to 17) or $CH_3(CH_2)_n$ CH (n=0 to 17) or CH)$_2$, and includes a group having a double bond or a triple bond or both in the chain, and further a branched or cyclized group,
Ri is $(CH_2)_n$ (n=0 to 17) or CH $(CH_2)_n$ CH (n=0 to 17), and includes a group having a double bond a triple bond or both in the chain, and further a branched or cyclized group,
RI is H or $CH_3(CH_2)_n$ CH (n=0 to 17) or $CH_3(CH_2)_n$ CH (n=0 to 17) or $CH_2$ or $CH_3(CH_2)_n$ C (n=0 to 17) or CH, and includes a group having a double bond or a triple bond or both in the chain, and further a branched or cyclized group;

NRkN:
Rk is $C(CH_2)_nC$ (n=0 to 17), and includes a group having a double bond or a triple bond or both in the chain, and further a branched or cyclized group.

In the present invention, a compound containing sulfur can be used as a monomer material. Examples of the compound containing sulfur include hydrogen sulfide; carbon disulfide thiophene; compounds of formula $CH_3S(CH_2)_nCH_3$ (n=0 to 17) such as dimethyl sulfide $(CH_3)_2S$; compounds of formula $CH_3(CH_2)_nSS(CH_2)_mCH_3$ (n=0 to 17, m=0 to 17) such as methyl disulfide $CH_3SSCH_3$; compounds of formula $CH_3(CH_2)_nSH$ (n=O to 17) such as ethanethiol $CH_3CH_2SH$; compounds of formula $SH(CH_2)_nSH$ (n=1 to 17) such as ethanedithiol $SH(CH_2)_2SH$; mercaptoethanol; and dithreitol.

Furthermore, compounds having one of or two or more of groups including —COOH, —CHO, —SH, —NH$_2$, —OH, =NH, CONH$_2$, —NCO, —CH=CH$_2$, =C=O and

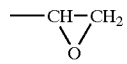

can be used as a monomer material. Examples of such compounds include cysteine, glutathione, formyl succinate, aminobenzoate, aminohexanate, mercaptobenzoate, and compounds having —C≡CCH$_2$OH.

In the present invention, a compound containing a halogen can be used as a monomer material. Examples of the compound containing a halogen for a plasma polymerization layer include tetrafluoroethylene, chlorobenzene, hexachlorobenzene, hexafluorobenzene, and vinyl fluoride.

In the present invention, an organic metal compound can be used as a monomer material. Examples of an organic metal compound for the plasma polymerization layer include an organic silicon compounds such as tetramethylsilane, tetramethyldisiloxane, hexamethyldisiloxane, hexamethyldisilazane, hexamethylcyclotrisilazane, dimethylaminotrimethylsilane, trimethylvinylsilane, tetramethoxysilane, aminopropyltriethoxysilane, octadecyldiethoxymethylsilane, hexamethyldisilane and divinyltetramethyldisiloxane.

Compounds of formulae (I) and (II) having no double bond or triple bond are preferably used because a layer is formed slowly so that the resulting layer is more homogeneous, compared with compounds having double bonds or triple bonds.

The thickness of plasma polymerization layer 3 is preferably 100 to 3000 angstroms, most preferably 500 to 1000 angstroms.

Plasma polymerization layer 3 can be formed by plasma treatment to a resulting plasma layer with a polymeric or non-polymeric monomer. Examples of such non-polymeric monomer material include nitrogen, ammonium, hydrazine, hydrogensulfide, hydrogendisulfide, oxygen, hydrogen, water, halogen gas, and rare gas (e.g., argon, neon, helium, krypton, and xenon).

Furthermore, a mixture of various kinds of monomer materials can be used as a monomer material. Plasma polymerization layer 3 can also be formed by lamination techniques and optionally using a mixture as a monomer material.

Plasma polymerization layer 3 of the present invention has the following advantages:

1) The layer is pinhole-free, amorphous, and dense.
2) A thin homogeneous layer down to about 500 angstroms can be made, which exhibits extremely little fluctuation in its refractive index.
3) By changing the kind of plasma gas, not only a change in the thickness of the layer but also surface modification and surface improvement, such as introduction of functional groups, and control of the density of the functional groups to be introduced can be attained.
4) The layer can be formed in combination with semiconductor techniques since it is formed under dry conditions.
5) The layer has excellent drug tolerance, heat tolerance, mechanical properties, and stability.

Furthermore, in the case of a sensor chip for SPR, in which a metal thin-film is essential, the metal thin-film and the plasma polymerization layer can be formed in the same chamber. Thus, the manufacturing process can be simplified.

It is also advantageous to attain surface improvement, such as introduction of a functional group, by further exposing a resulting plasma polymerization layer to plasma treatment with a non-polymeric or polymeric monomer. The plasma polymerization treatment is intended to include a treatment with not only a non-polymeric monomer and an inactive monomer but also a polymeric monomer.

Physiologically active substance 4 to be immobilized is not particularly limited, provided it reacts interacts with a target substance to be measured. Examples of physiologically active substance 4 include nucleic acids (e.g., DNA, RNA, and PNA); non-immune proteins (e.g., avidin (streptoavidin), biotin or a receptor); immunoglobulin-binding proteins (e.g., protein A, protein G and a rheumatoid factor (RF)); sugar-binding proteins (e.g., lectin); sugar-recognizing sugar chains; fatty acids or fatty acid esters (e.g., stearic acid, alachidic acid, behenic acid, ethyl stearate, ethyl arachidate, and ethyl behanate); polypeptides or oligopeptides having ligand binding activity; immune proteins (e.g., an antibody); and enzyme.

Figure 3:
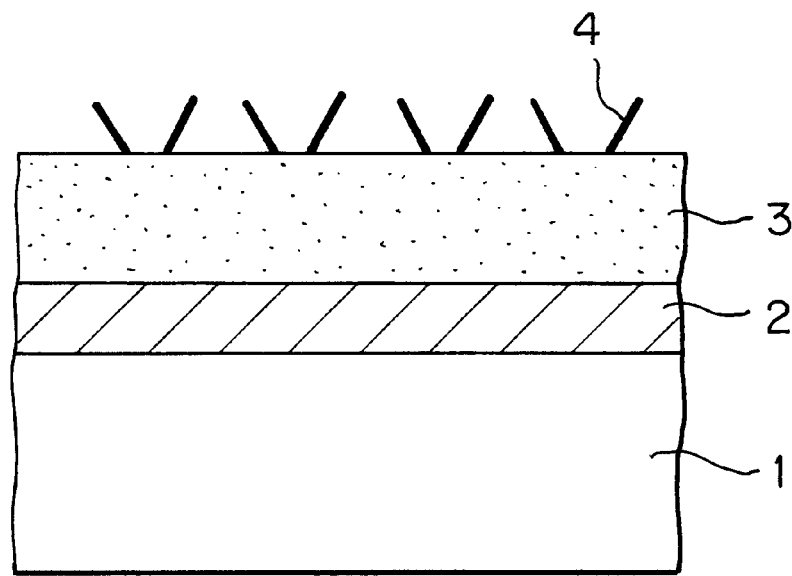
FIGS. 3(a) and (b) each show a schematic sectional view of an optical part of a measuring chip for a surface plasmon resonance biosensor. (a) shows immobilization of an Fab fragment of an antibody. (b) shows immobilization of an F(ab')$_2$ fragment of an antibody. 1: Transparent substrate; 2: Metal thin-film; 3: Plasma polymerization layer; 4: Physiologically active substance.
Figure 3:
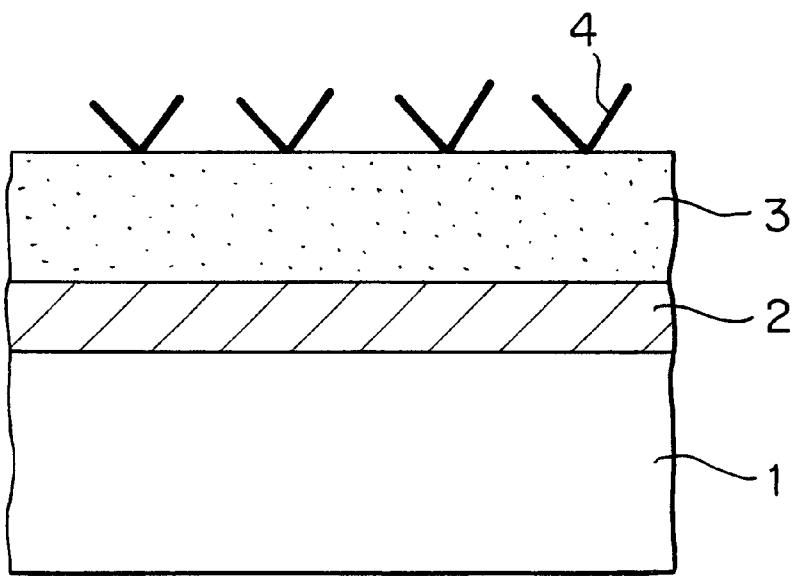

When an antibody is used as physiologically active substance 4, Fc fragments of the antibody can be immobilized only on the surface of plasma polymerization layer 3 and the antibody is formed in a monomolecular layer as shown in FIG. 1. However, since the sensitivity and the reaction rate decrease as Fab fragments of the antibody are separated from plasma polymerization layer 3, Fab fragments (FIG. 3(a)) or F(ab')$_2$ fragments (FIG. 3(b)) can be immobilized directly on plasma polymerization layer 3 as shown in FIG. 3 to improve the sensitivity and the reaction rate.

The thickness of physiologically active substance 4 depends on the size of the physiologically active substance itself, but is preferably 100 to 3000 angstroms, most preferably 100 to 1000 angstroms.

In the present invention, the physiologically active substance can be immobilized on the plasma polymerization layer through linking agents.

Figure 4:
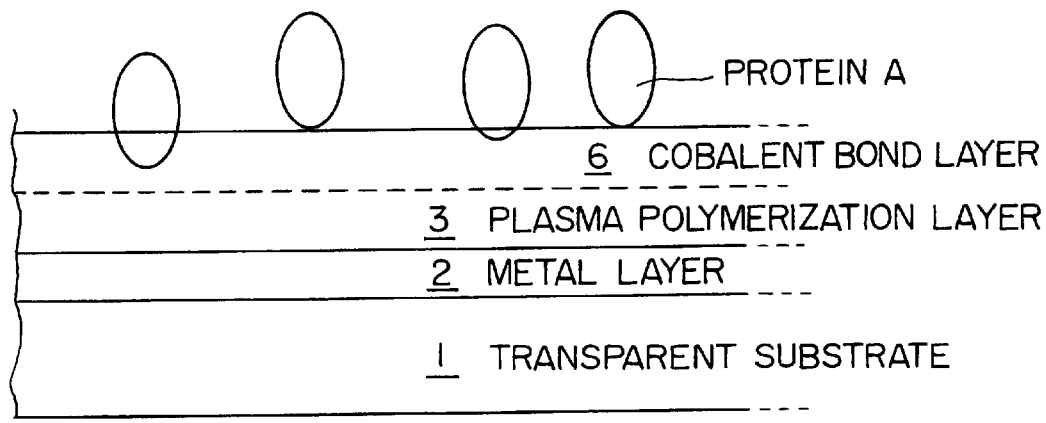
FIG. 4 is a schematic sectional view of an optical part of a measuring chip for a surface plasmon resonance biosensor.

FIG. 4 is a schematic illustration showing one embodiment of the measuring chip according to the present invention. The measuring chip has covalent bond layer 6 between plasma polymerization layer 3 and physiologically active substance 4. Substance 4 is immobilized on plasma polymerization layer 3 via covalent layer 6. The covalent bond can be formed with a cross-linking reagent or a condensation reagent.

The cross-linking reagent or a condensation reagent is not particularly restricted, provided it can covalently and firmly immobilize substance 4. They can be used alone or in combination.

Examples of such cross-linking reagents include glutaraldehyde, periodic acid, N-succinimidyl-2-maleimidoacetic acid, N-succinimidyl-4-maleimidobutyric acid, N-succinimidyl-6-maleimidohexanic acid, N-succinimidyl-4-maleimidomethylcyclohexan-1-carboxylic acid, N-sulfosuccinimidyl-4-maleimidomethylcyclohexane-1-carboxylic acid, N-succinimidyl-4-maleimidomethylbanzoic acid, N-succinimidyl-3-maleimidobenzoic acid, N-sulfosuccinimidyl-3-maleimidobenzoic acid, N-succinimidyl-4-maleimidophenyl-4-butyric acid, N-sulfosuccinimidyl-4-maleimidophenyl-4-butyric acid, N,N'-oxydimethylene-dimaleimide, N,N'-o-phenylene-dimaleimide, N,N'-m-phenylene-dimaleimide, N,N'-p-phenylene-dimaleimide, N,N'-hexamethylene-dimaleimide, N-succinimidylmaleimidocarboxylic acid, N-succinimidyl-S-acetylmercaptoacetic acid, N-succinimidyl-3-(2-pyridyldithio)propionate, S-acetylmercaptosuccinic anhydride, methyl-3-(4'-dithiopyridyl)propionimidate, methyl-4-mercaptobutylimidate, methyl-3-mercaptopropionimidate, iminothiolene, o-carboxymethyl-hydroxylamine, azodiphenylpilmaleido, bis(sulfosuccinimidyl)sperate, 4,4'-diisothiocyano-2,2'-disulfonic acid stilbene, 4,4'-difluoro-3,3'-dinitrodiphenylsulfon, 1,5-difluoro-2,4-dinitrobenzene, p-phenylenediisothiocyanate, dimethyladipimidate, dimethylpimelimidate, dimethylsuberimidate, p-azidophenacylbromide, p-azidophenylglyoxal, N-hydroxysuccinimidyl-4-azidobenzoate, 4-fluoro-3-nitrophenylazide, methyl-4-azidobenzoimidate, N-5-azido-2-nitrobenzoyloxysuccinimide, N-succinimidyl-6-(4'-azido-2'-nitrophenylamino)hexanoate, 1,4-benzoquinone, N-succinimidyl-3-(2'-pyridyldithio)propionate, N-(4-maleimidobutyloxy)sulfosuccinimide sodium salt, N-(6-nmaleimidocaproyloxy)sulfosuccinimide sodium salt, N-(8-maleimidocaproyloxy)sulfosuccinimide sodium salt, N-(8-maleimidoundecanoyloxy)sulfosuccinimide sodium salt, N-[2-(1-piperazinyl)ethyl]maleimide bichloric acid, bisdiazobenzidine, hexamethylenediisocyanate, toluenediisocyanate, hexamethylenediisothiocyanate, N,N'-ethylenebismaleinimide, N,N'-polymethylenebisiodoacetamide, 2,4-dinitrobenzenesulfonate sodium salt, and diazo compounds. Glutaraldehyde is preferable as a cross-linking reagent.

Examples of such condensation reagents include carbodiimide derivatives represented by formula RN=C=NR (or R'), N-hydroxysuccinimide, tri-n-butylamine, butyl chloroformate, and isobutyl isocyanide.

By introducing covalent layer 6 to the measuring cell to firmly mobilize physiologically active substance 4 via covalent bonds, substance 4 can be maintained immobilized when the measuring cell is washed, which enables the cell to be used for repetitive measurements for another advantageous feature. The thickness of covalent layer 6 is preferably 10 to 100 angstroms, most preferably 10 to 20 angstroms.

The physiologically active substance can also be immobilized by hydrophobic bond, by integrating substance 4 into a plasma polymerization layer or by an additional plasma treatment.

A preferred group of the measuring chip according to the present invention is a measuring chip comprising a metal layer, one or more plasma polymerization layers formed on said metal layer, and an immune protein or enzyme immobilized on the surface of said plasma polymerization layer, wherein said plasma polymerization layer comprises a monomer material selected from the group consisting of pyridine, triethylamine, diethylamine, allylamine, acrylamide, aniline, acrylonitrile, 1,2,4-triazole, 5-amino-1H-tetrazole, and acetonitrile.

Another preferred group of the measuring chip according to the present invention is a measuring chip comprising a metal layer, one or more plasma polymerization layers formed on said metal layer, and an immune protein or enzyme immobilized on the surface of said plasma polymerization layer, wherein said plasma polymerization layer comprises a monomer material selected from the group consisting of pyridine, triethylamine, diethylamine, allylamine, acrylamide, aniline, acrylonitrile, 1,2,4-triazole, 5-amino-1H-tetrazole, and acetonitrile and wherein said immune protein or enzyme is immobilized on said plasma polymerization layer through a cross-linking reagent or a water-soluble condensation reagent.

A cross-linking reagent for the preferred group above can be selected from the group consisting of glutaraldehyde, N-succinimidyl-4-maleimidomethylbanzoic acid, N-succinimidyl-3-maleimidobenzoic acid, N-succinimidyl-4-maleimidophenyl-4-butyric acid, N,N'-oxydimethylene-dimaleimide, N,N'-m-phenylene-dimaleimide, N,N'-p-phenylene-dimaleimide, N,N'-35 hexamethylene-dimaleimide, N-succinimidylmaleimidocarboxylic acid, N-succinimidyl-S-acetylmercaptoacetic acid, N-succinimidyl-3-(2-pyridyldithio)propionate, S-acetylmercaptosuccinic anhydride, methyl-3-(4'-dithiopyridyl)propionimidate, methyl-4-mercaptobutylimidate, methyl-3-mercaptopropionimidate, iminothiolene, o-carboxymethyl-hydroxylamine, azodiphenylpilmaleido, 5 bis(sulfosuccinimidyl)sperate, 4,4'-diisothiocyano-2,2'-disulfonic acid stilbene, 4,4'-difluoro-3,3'-dinitrodiphenylsulfon, 1,5-difluoro-2,4-dinitrobenzene, p-phenylenediisothiocyanate, dimethyladipimidate, dimethylpimelimidate, dimethylsuberimidate, p-azidophenacylbromide, p-azidophenylglyoxal, N-hydroxysuccinimidyl-4-azidobenzoate, 4-fluoro-3-nitrophenylazide, methyl-4-azidobenzoimidate, N-5-azido-2-nitrobenzoyloxysuccinimide, N-succinimidyl-6-(4'-azido-2'-nitrophenylamino)hexanoate, 1,4-benzoquinone, N-succinimidyl-3-(2'-pyridyldithio)propionate, bisdiazobenzidine, hexamethylenediisocyanate, toluenediisocyanate, hexamethylenediisothiocyanate, N,N'-ethylenebismaleinimido, N,N'-polymethylenebisiodoacetoamide, and diazo compounds; or said condensation reagent is one or more compounds selected from the group consisting of carbodiimide derivatives represented by RN=C=NR (or R'), N-hydroxysuccinimide, tri-n-butylamine, butyl chloroformate, and isobutyl isocyanide.

The measuring chip according to the present invention can be formed as follows:

First, metal thin-film 2 is formed on transparent substrate 1. Metal thin-film 2 can be formed by conventional methods such as sputtering, CVD, PVD, or vacuum evaporation.

Second, plasma polymerization layer 3 is formed on metal thin-film 2. Plasmapolymerization layer 3 can be formed by plasma polymerization using a plasma polymerization apparatus. The rate of plasma formation is preferably 100 to 3000 angstroms/min, most preferably 500 to 1000 angstroms/min. If the rate exceeds 3000 angstroms/min, it becomes difficult to obtain a smooth plasma polymerization layer. More specifically, the plasma polymerization can be preferably carried out at a monomer material flow rate of 0.05 to 100 sccm at a room temperature or at a temperature of 10 to 20C. at a pressure between $1.0 \times 10^{-2}$ and $1.0 \times 10^2$ Pa using a discharge power of 20 to 300 W at a discharge frequency of 10 MHz or 13.56 MHz. However, polymerization conditions are not restricted to the conditions above.

After formation of plasma polymerization layer 3, physiologically active substance 4 is finally immobilized on plasma polymerization layer 3. Immobilization can be done by conventional methods. For example, a specified amount of physiologically active substance 4 can be immobilized by contacting it with plasma polymerization layer 3 for a specified period of time. If the measuring cell is a flow-cell type, a specified volume of the physiologically active substance 4 can be immobilized by contacting it with plasma polymerization layer 3 by pouring a specified volume for a specified period of time.

When an antibody is used as a physiologically active substance and its Fab fragment is immobilized directly on plasma polymerization layer 3, the same treatment can be done after the antibody is partly digested with papain. On the other hand, when the $F(ab')_2$ fragment is immobilized directly on plasma polymerization layer 3, the same treatment can be done after the antibody is partly digested with pepsin.

When covalent bond layer 6 is formed, a cross-linking reagent or a condensation reagent is allowed to be in contact with plasma polymerization layer 3 in the same manner as with active substance 4, after which substance 4 can be immobilized.

The measuring cell for a surface plasmon resonance sensor according to the present invention comprises the measuring chip. The measuring chip can be mounted on an optical part to be optically analyzed. The term "optical part" as used herein refers to a part where a light is projected and an evanescent wave and a surface plasmon can be induced.

The surface plasmon resonance biosensor according to the present invention comprises the measuring cell.

Figure 5:
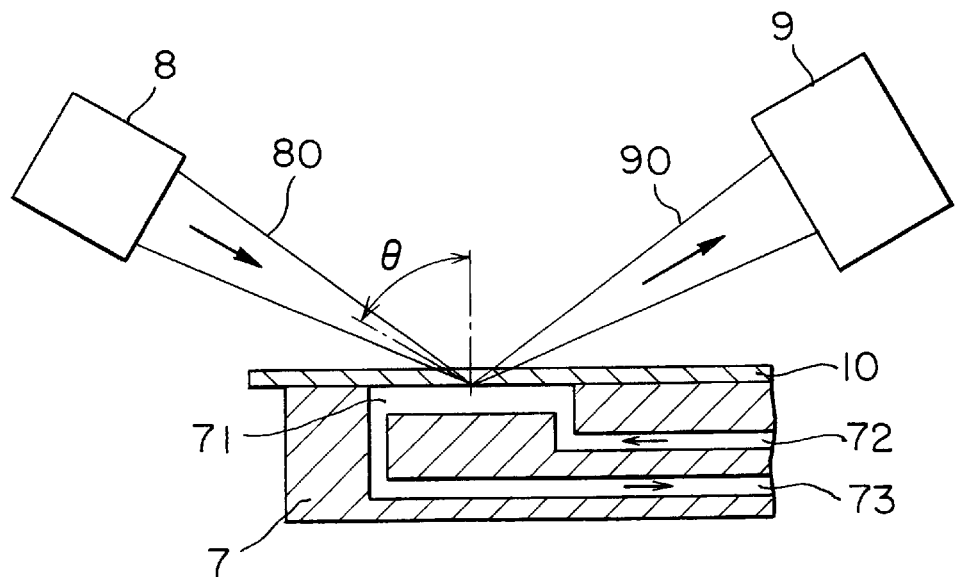
FIG. 5 illustrates a surface plasmon resonance biosensor. 7: Cartridge block; 8: Light source; 9: Detector; 10: Measuring chip; 71: Measuring cell; 72, 73: Flow routes; 80: Incident light; 90: Reflecting light.

FIG. 5 is a schematic view of one embodiment of the surface plasmon resonance biosensor according to the present invention. The surface plasmon resonance biosensor has cartridge block 7, light source 8, and detector 9 and measuring chip 10 is mounted on cartridge block 7. The upper side of cartridge block 7 has a hollow and this hollow and measuring chip 10 construct measuring cell 71.

The body of measuring chip 10 comprises a transparent substrate, and a layer comprising a metal thin-film, a plasma polymerization layer formed under said metal film. A physiologically active substance is immobilized on the surface of said plasma polymerization layer facing the hollow of cartridge block 7. Measuring cell 71 is constructed from the hollow of cartridge block 7 and measuring chip 10; and cartridge block 7 has flow routes 72 and 73 providing passages to the outside of measuring cell 71 and cartridge block 7, which makes measuring cell 71 a flow-cell type. However, the present invention is not restricted to this type and a batch type cell can also be used. Using measuring cell 71 of this flow-cell type, a sample can be measured either continuously or intermittently. In this sensor, the sample flows into measuring cell 71 via flow route 72 and is discharged after measurement via flow route 73. The flow rate of the sample is preferably 0.5 to 5 $\mu$l/min. The flow rate is controlled, for example, using a computer-operated pump.

Monochromatic light (incident light 80) is irradiated from light source 8 toward the optical part of measuring chip 10 and its reflected light 90, which is reflected by metal thin-film 2 set on the reverse side of measuring chip 10, reaches detector 9. Detector 9 can detect the intensity of reflected light 90. Light source 8 and detector 9 are not particularly restricted, and can be any types customarily used for a surface plasmon resonance biosensor. In the sensor according to the present invention, the incident light is wedge-shaped and the light reflected in different directions can be measured simultaneously. However, the present invention is not restricted to this type of sensor. The configuration of this type does not require a mobile part, thereby producing excellent stability and durability, and enabling real time measurement of samples as well.

Figure 6:
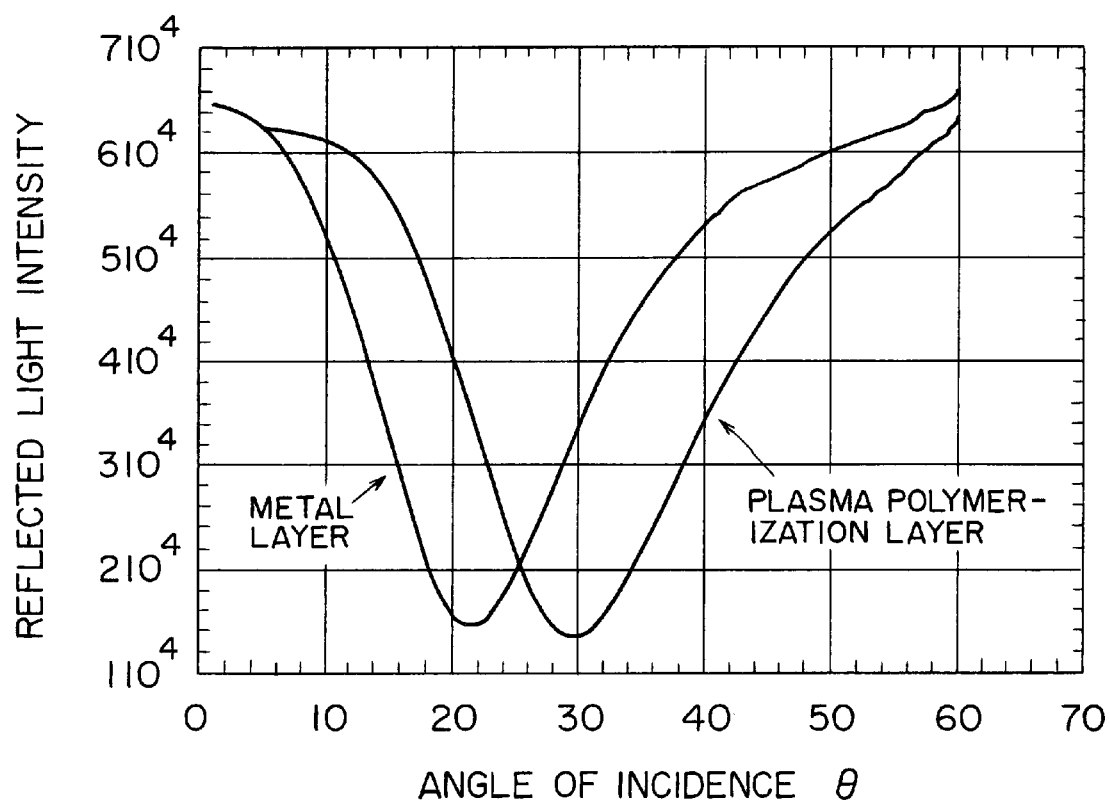
FIG. 6 illustrates a reflected light intensity curve before and after plasma polymerization membrane formation.

The configuration as described above yields a reflected light intensity curve that forms a trough relative to a given angle of incidence (see FIG. 6). The trough in the reflected light intensity curve is due to surface plasmon resonance. Namely, when light is totally reflected at the interface between the transparent substrate and the exterior of measuring chip 10, a surface wave known as an evanescent wave is generated at the interface and a surface wave known as a surface plasmon is also generated on the metal thin-film. Resonance occurs when the wave number of these two surface waves coincides and a part of light energy is consumed to excite the surface plasmon, resulting in a decrease in the intensity of the reflected light. The wave number of the surface plasmon is affected by the refractive index of the medium proximate to the surface of the metal thin-film. Therefore, when the refractive index of the medium changes due to an interaction between the substance to be measured and the physiologically active substance, a surface plasmon resonance is induced to change the angle of incidence. Thus, a change in the concentration of the substance to be measured can be perceived by a shift of the trough in the reflected light intensity curve. The change in the angle of incidence is called a resonance signal and a change of $10^{-4}$ degree is expressed as 1 RU. In the surface plasmon resonance biosensor of this example, highly effective and reliable measurement can be done if measuring chip 10 is made to be freely attachable and detachable and disposable. Furthermore, if a covalent bond layer is provided between the plasma polymerization layer and the physiologically active substance, measuring chip 10 can be used repeatedly by washing the inside of measuring cell 71, resulting in a decrease in the cost.

The surface plasmon resonance biosensor of the present invention can be used for quantitative or qualitative analysis, identification of a target substance present in a sample.

EXAMPLE

The present invention is further illustrated by the following Examples that are not intended as a limitation of the invention.

Example 1

A measuring chip having layers shown in FIG. 1 on an optical recognition part was constructed.

A glass plate with a thickness of 0.15 mm (18 mm×18 mm) was used for a transparent substrate. A chrome layer and then a gold layer were deposited on this transparent substrate by sputtering. The sputtering was carried out at 100 W for 40 seconds for the chrome layer and at 100 W for 2 minutes and 30 seconds for the gold layer. The resulting chrome layer was 40 angstroms thick and the resulting gold layer was 500 angstroms thick.

Figure 7:
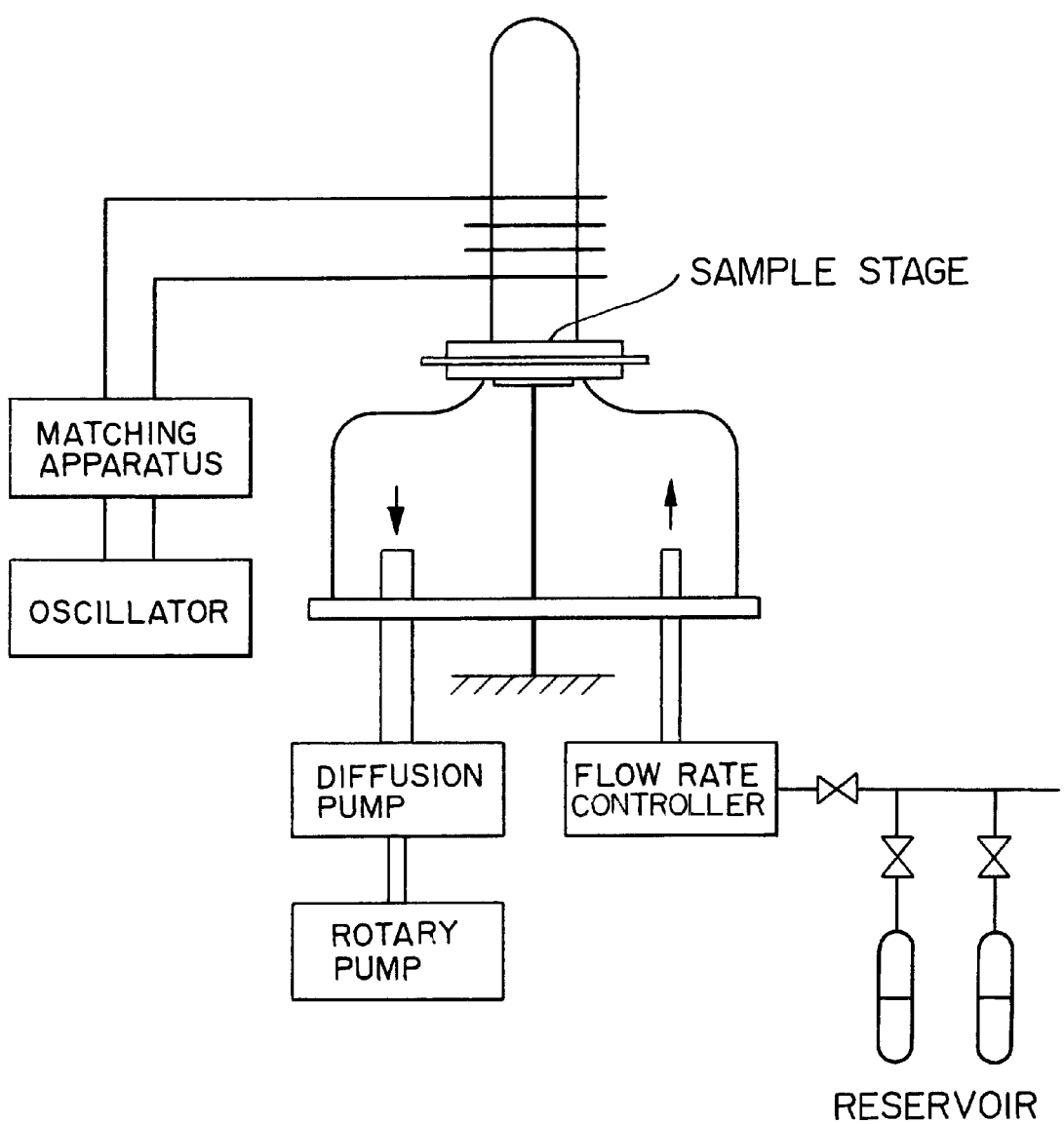
FIG. 7 illustrates a schematic view showing the apparatus used in Example 1.
Figure 12:
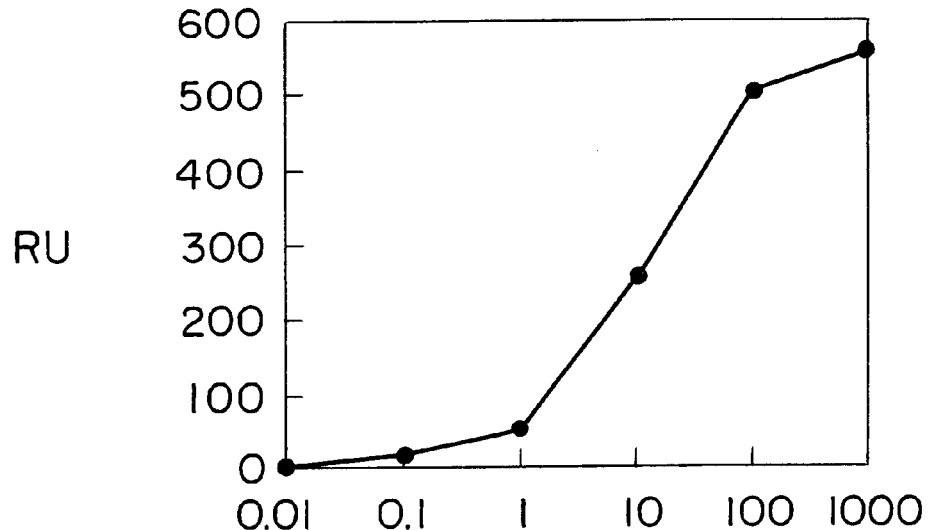
FIG. 12 shows the relationship between the concentration of the HSA antigen and RU in Example 5.
Figure 13:
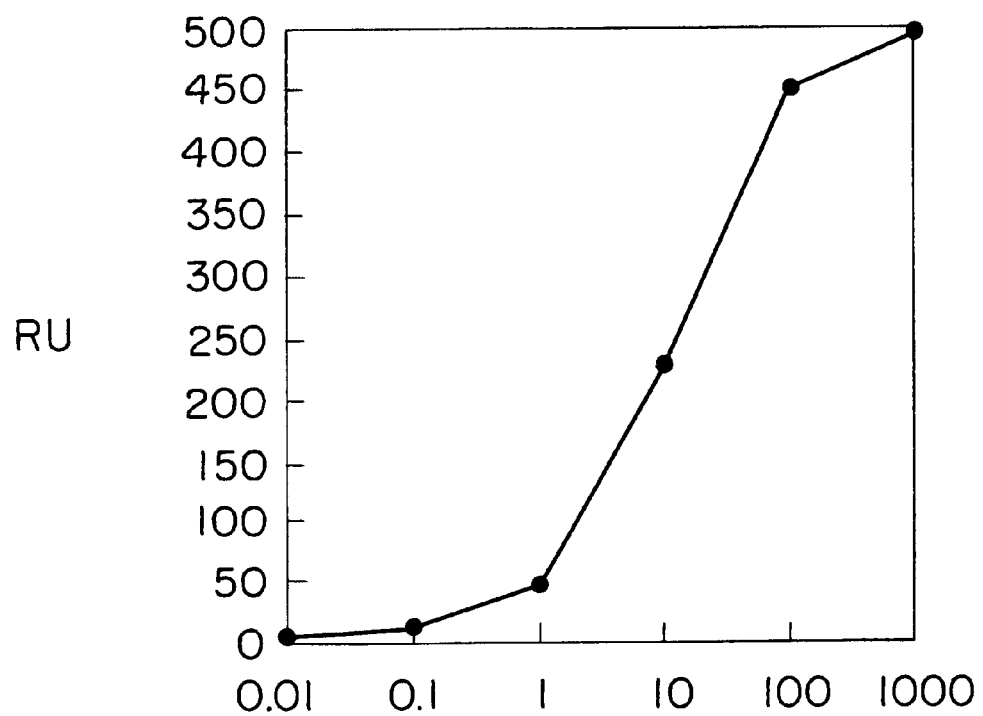
FIG. 13 shows the relationship between the concentration of the BSA antigen and RU in Example 6.
Figure 18:
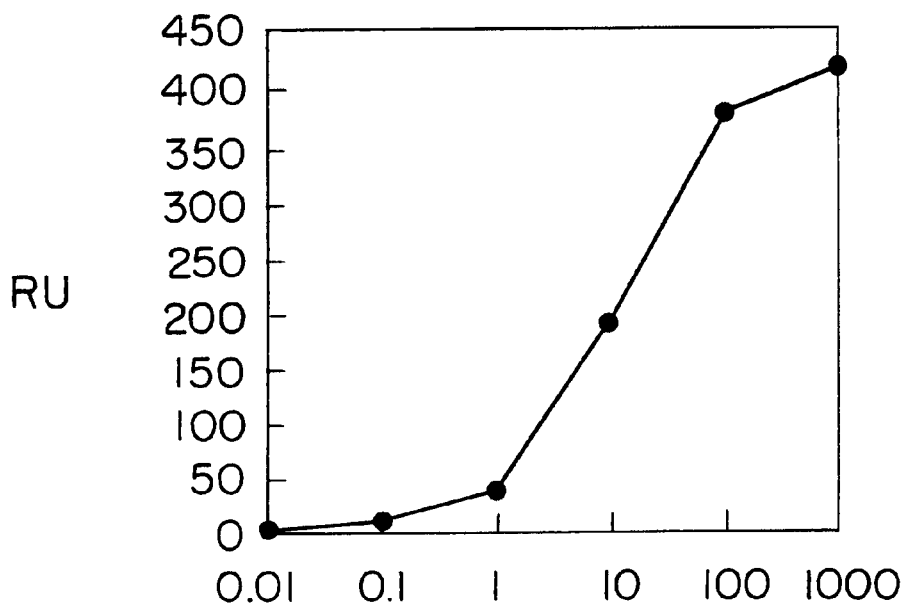
FIG. 18 shows the relationship between the concentration of the BSA antigen and RU in Example 11.
Figure 19:
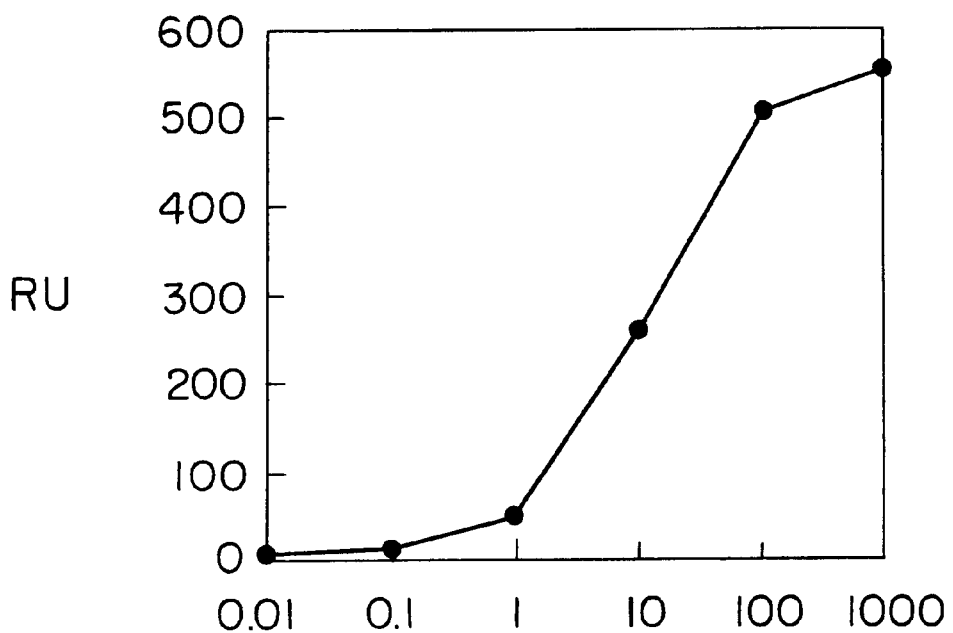
FIG. 19 shows the relationship between the concentration of the HSA antigen and RU in Example 12.
Figure 20:
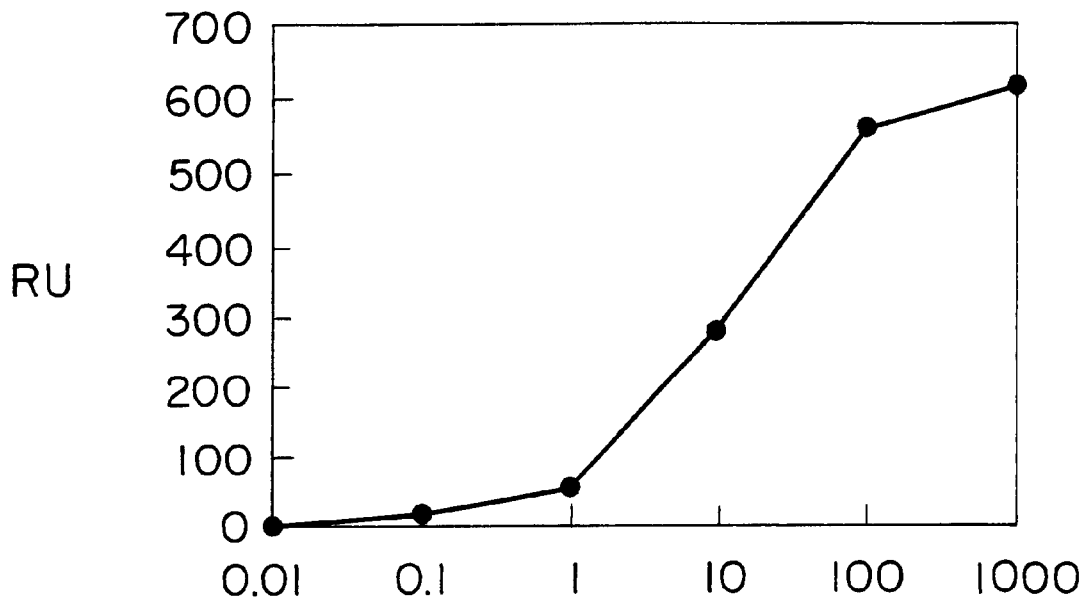
FIG. 20 shows the relationship between the concentration of the HSA antigen and RU in Example 13.
Figure 21:
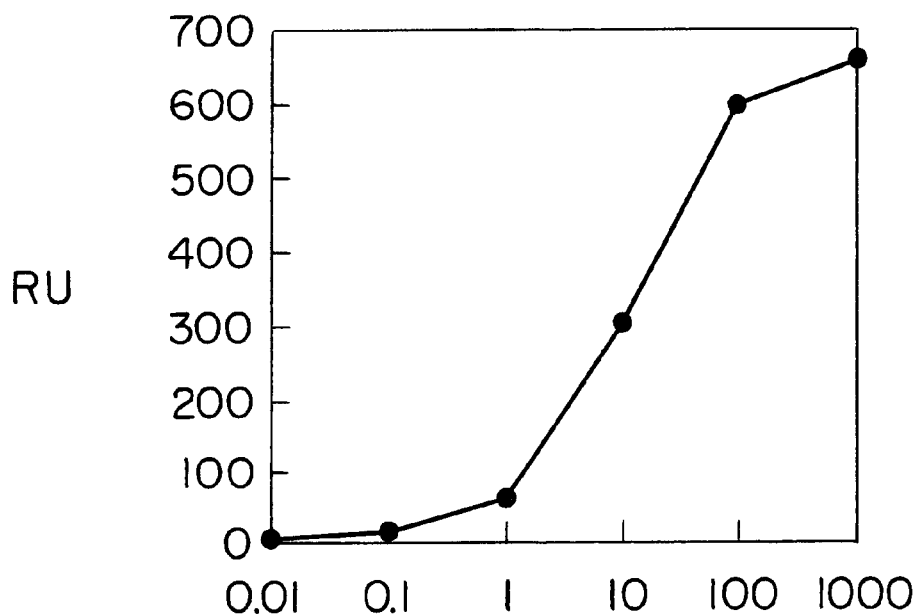
FIG. 21 shows the relationship between the concentration of the HSA antigen and RU in Example 14.
Figure 26:
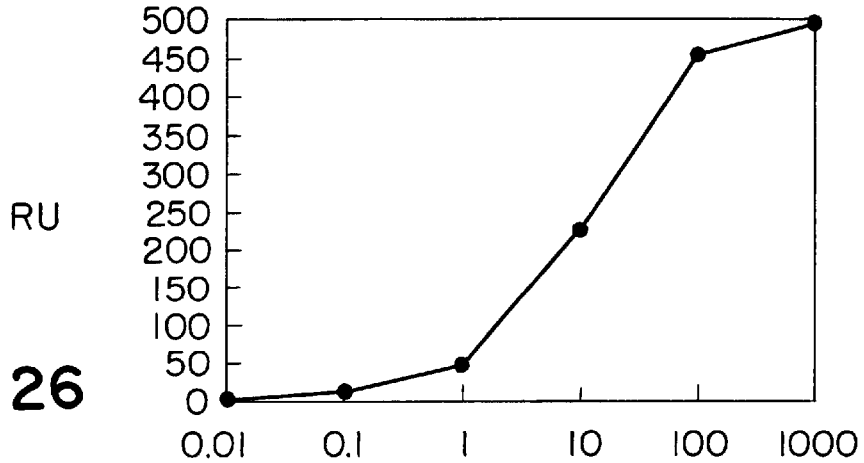
FIG. 26 shows the relationship between the concentration of skatole and RU in Example 19.
Figure 27:
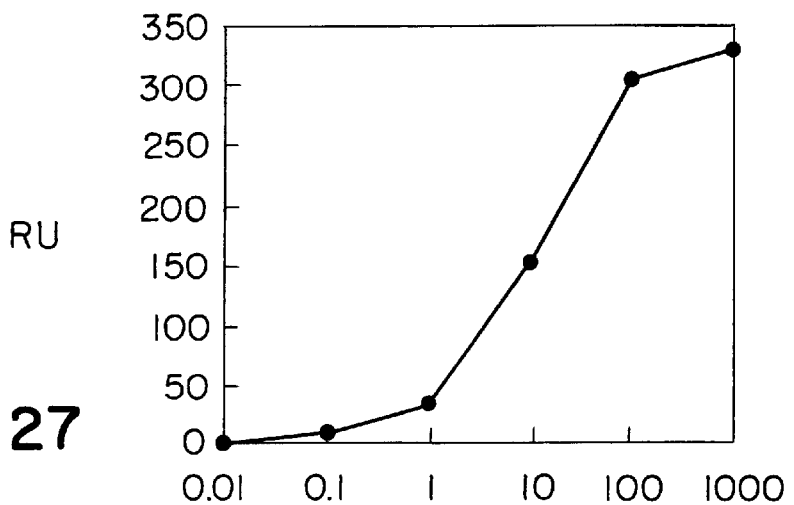
FIG. 27 shows the relationship between the concentration of the HSA antigen and RU in Example 20.
Figure 28:
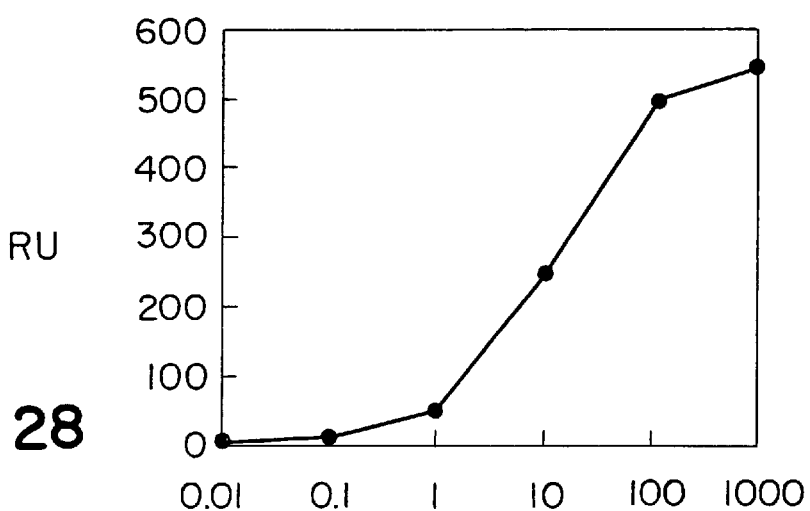
FIG. 28 shows the relationship between the concentration of the HSA antigen and RU in Example 21.

A plasma polymerization layer was formed on the metal layers. An apparatus as shown in FIG. 7 was used for plasma polymerization. Ethanedithiol was used as a monomer material for the plasma polymerization layer to introduce a thiol group. Conditions for plasma polymerization were as follows:

Flow volume of monomer material: 15 sccm
Temperature: 15° C.
Pressure: 4.7 Pa
Discharge electric power: 20 W
Discharge frequency: 10 MHz, FM modulation
Duration of discharge: 60 seconds.

Under the conditions described above, a thiol group was introduced on the surface of plasma polymerization layer. The sensor chip with the introduced thiol group was mounted on the cartridge block of the surface plasmon resonance biosensor and maleimidized avidin (see "Ultrahigh Sensitivity Enzyme Immunoassay" by Eiji Ishikawa) was poured through a flow route into the measuring cell at a flow rate of 5 µl/min for immobilization on the thiol group on the plasma polymerization layer for 60 minutes. 50 µl of 10 µM-biotinized DNA were then poured and the probe DNA was immobilized via the avidin for 10 minutes. A DNA ($7.5 \times 10^{-7}$ M) having a DNA sequence complementary to this probe DNA was introduced and after the reaction, a signal of about 500 RU was obtained.

| Concentration of Complementary DNA (µM) | 0.00075 | 0.0075 | 0.075 | 0.75 | 7.5 | 75 |
|---|---|---|---|---|---|---|
| RU | 10 | 25 | 100 | 500 | 1000 | 1100 |

It was confirmed by an XPS analysis that the resulting membrane has a mercapto group.

FIG. 6 shows the reflected light intensity curve before and after the formation of the plasma polymerization layer, which show the intensity of reflected light corresponding to the angle of incidence θ). FIG. 6 shows that the plasma polymerization layer is formed on the surface of the gold layer. The thickness of the plasma polymerization layer can be estimated from Δθ.

Example 2

The same apparatus and method as in Example 1 were used.

Acetonitrile was used as a monomer material for the plasma polymerization layer. Conditions for plasma polymerization were as follows:

Flow volume of monomer material: 1.5 sccm+Ar dilution 15 (sccm)
Temperature: room temperature
Pressure: 4.7 Pa
Discharge electric power: 80 W
Discharge frequency: 13.56 MHz
Duration of discharge: 15 seconds.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 µl/min for 10 minutes and avidin (concentration: 20 µg/ml) was also poured at a flow rate of 5 µl/min to immobilize for 60 minutes. 10 µM biotin-labeled probe RNA were then poured at a flow rate of 1 µl/min to immobilize the probe RNA for 10 minutes. DNA ($7.5 \times 10^{-7}$ M) having a DNA sequence complementary to this probe RNA was introduced and after the reaction, a signal of about 500 RU was obtained.

| Concentration of Complementary DNA (μM) | 0.00075 | 0.0075 | 0.075 | 0.75 | 7.5 | 75 |
|---|---|---|---|---|---|---|
| RU | 8 | 20 | 80 | 400 | 800 | 880 |

It was confirmed by the XPS analysis that the resulting membrane has a primary amine.

Example 3

The same apparatus and method as in Example 1 were used.

Conditions for plasma polymerization layer formation were the same as in Example 2.

Under the conditions described above, a plasma polymerization layer was formed.

The sensor chip was mounted on the cartridge block of the surface plasmon resonance biosensor, 5% glutaraldehyde was poured through a flow route into the measuring cell at a flow rate of 5 μl/min for 10 minutes and streptoavidin (concentration: 20 μg/ml) was also poured at a flow rate of 5 μl/min to immobilize for 60 minutes. 10 μM biotin-labeled probe RNA was then poured at a flow rate of 1 μl/min for 10 minutes to immobilize the probe RNA. DNA (7.5×10$^{-7}$ M) having a DNA sequence complementary to this probe RNA was introduced and after the reaction, a signal of about 375 RU was obtained.

| Concentration of Complementary DNA (μM) | 0.00075 | 0.0075 | 0.075 | 0.75 | 7.5 | 75 |
|---|---|---|---|---|---|---|
| RU | 7.5 | 18.75 | 75 | 375 | 750 | 825 |

It was confirmed by the XPS analysis that the resulting membrane has a primary amine.

Example 4

The same apparatus and method as in Example 1 were used.

Conditions for plasma polymerization layer formation were the same as in Example 2 except that propargylamine was used as a monomer material.

Under the conditions described above, a plasma polymerization layer was formed. The sensor chip was mounted on the cartridge block of the surface plasmon resonance biosensor, 0.4 M N-ethyl-N'-25 (3-dimethylaminopropyl) carbodiimide was poured through a flow route into the measuring cell at a flow rate of 5 μl/min for 10 minutes and avidin (concentration: 20 μg/ml) was also poured at a flow rate of 5 μl/min to immobilize for 60 minutes. 10 μM biotin-labeled probe RNA was then poured at a flow rate of 1 μl/min 30 for 10 minutes to immobilize the probe RNA. DNA(7.5×10$^{x7}$ M) having a DNA sequence complementary to this probe RNA was introduced and after the reaction, a signal of about 450 RU was obtained.

| Concentration of Complementary DNA (μM) | 0.00075 | 0.0075 | 0.075 | 0.75 | 7.5 | 75 |
|---|---|---|---|---|---|---|
| RU | 0.9 | 22.5 | 90 | 450 | 900 | 990 |

It was confirmed by the XPS analysis that the resulting membrane has a primary amine.

Example 5

The same apparatus and method as in Example 1 were used.

Conditions for plasma polymerization layer formation were the same as in Example 4.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 μl/min for 10 minutes and protein A (concentration: 400 μg/ml) was also poured at a flow rate of 5 μl/min to immobilize for 60 minutes. An anti-HSA antibody (concentration: 400 μl/ml) was then poured at a flow rate of 1 μl/min for 10 minutes to immobilize the antibody. An HSA antigen (10 μg/ml) complementary to this anti-HSA antibody was introduced and after the reaction, a signal of about 250 RU was obtained.

| Concentration of HSA antigen (μg/ml) | 0.01 | 0.1 | 1 | 10 | 100 | 1000 |
|---|---|---|---|---|---|---|
| RU | 5 | 12.5 | 50 | 250 | 500 | 550 |

It was confirmed by the XPS analysis that the resulting membrane has a primary amine.

Example 6

The same apparatus and method as in Example 1 were used.

Conditions for plasma polymerization layer formation were the same as in Example 4.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 μl/min for 10 minutes and protein G (concentration: 400 μg/ml) was also poured at a flow rate of 5 μl/min to immobilize for 60 minutes. An anti-BSA antibody (concentration: 400 μl/ml) was then poured at a flow rate of 1 μl/min for 10 minutes to immobilize the antibody. A BSA antigen (10 μg/ml) complementary to this anti-BSA antibody was introduced and after the reaction, a signal of about 225 RU was obtained.

| Concentration of BSA antigen (μg/ml) | 0.01 | 0.1 | 1 | 10 | 100 | 1000 |
|---|---|---|---|---|---|---|
| RU | 4.5 | 11.25 | 45 | 225 | 450 | 495 |

It was confirmed by the XPS analysis that the resulting membrane has a primary amine.

Example 7

The same apparatus and method as in Example 1 were used.

Conditions for plasma polymerization layer formation were the same as in Example 4.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 μl/min for 10 minutes and mannose-binding lectin (concentration: 200 μg/ml) was also poured at a flow rate of 5 μl/min to immobilize for 60 minutes.

A sugar (10 μg/ml) complementary to this mannose-binding lectin was introduced and after the reaction, a signal of about 200 RU was obtained.

| Concentration of sugar (μg/ml) | 0.01 | 0.1 | 1 | 10 | 100 | 1000 |
|---|---|---|---|---|---|---|
| RU | 4 | 10 | 40 | 200 | 400 | 440 |

It was confirmed by the XPS analysis that the resulting membrane has a primary amine.

Example 8

The same apparatus and method as in Example 1 were used.

Conditions for plasma polymerization layer formation were the same as in Example 4 except that pyridine was used as a monomer material.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 μl/min for 10 minutes and an anti-BSA antibody (concentration:

400 μg/ml) was also poured at a flow rate of 5 μl/min to immobilize for 60 minutes. A BSA antigen (10 μg/ml) complementary to this anti-BSA antibody was introduced and after the reaction, a signal of about 187.5 RU was obtained.

| Concentration of BSA antigen (μg/ml) | 0.01 | 0.1 | 1 | 10 | 100 | 1000 |
|---|---|---|---|---|---|---|
| RU | 3.75 | 9.375 | 37.5 | 187.5 | 375 | 412.5 |

It was confirmed by the XPS analysis that the resulting membrane has a primary amine.

Example 9

The same apparatus and method as in Example 1 were used.

Conditions for plasma polymerization layer formation were the same as in Example 8 except that acrylonitrile was used as a monomer material.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 μl/min for 10 minutes and an anti-BSA antibody (concentration: 400 μg/ml) was also poured at a flow rate of 5 μl/min to immobilize for 60 minutes. A BSA antigen (10 μg/ml) complementary to this anti-BSA antibody was introduced and after the reaction, a signal of about 200 RU was obtained.

| Concentration of BSA antigen (μg/ml) | 0.01 | 0.1 | 1 | 10 | 100 | 1000 |
|---|---|---|---|---|---|---|
| RU | 4 | 10 | 40 | 200 | 400 | 440 |

It was confirmed by the XPS analysis that the resulting membrane has a primary amine.

Example 10

The same apparatus and method as in Example 1 were used.

Conditions for plasma polymerization layer formation were the same as in Example 9 except that ethanethiol was used as a monomer material.

Under the conditions described above, a plasma polymerization layer was formed. The sensor chip was mounted on the cartridge block of the surface plasmon resonance biosensor and maleimidized anti-BSA antibody was poured through a flow route at a flow rate of 5 μl/min to immobilize for 60 minutes. A BSA antigen (10 μg/ml) complementary to this anti-BSA antibody was introduced and after the reaction, a signal of about 200 RU was obtained.

| Concentration of BSA antigen (μg/ml) | 0.01 | 0.1 | 1 | 10 | 100 | 1000 |
|---|---|---|---|---|---|---|
| RU | 4 | 10 | 40 | 200 | 400 | 440 |

It was confirmed by the XPS analysis that the resulting membrane has a mercapto group.

Example 11

The same apparatus and method as in Example 1 were used.

Conditions for plasma polymerization layer formation were the same as in Example 10 except that thiophene was used as a monomer material.

Under the conditions described above, a plasma polymerization layer was formed. The sensor chip was mounted on the cartridge block of the surface plasmon resonance biosensor and maleimidized anti-BSA antibody was poured through a flow route at a flow rate of 5 µl/min to immobilize for 60 minutes. A BSA antigen (10 µg/ml) complementary to this anti-BSA antibody was introduced and after the reaction, a signal of about 187.5 RU was obtained.

| Concentration of BSA antigen (µg/ml) | 0.01 | 0.1 | 1 | 10 | 100 | 1000 |
|---|---|---|---|---|---|---|
| RU | 3.75 | 9.375 | 37.5 | 187.5 | 375 | 412.5 |

It was confirmed by the XPS analysis that the resulting membrane has a mercapto group.

Example 12

The same apparatus and method as in Example 1 were used.

Conditions for plasma polymerization layer formation were the same as in Example 11 except that acetonitrile was used as a monomer material.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 µl/min for 10 minutes and an anti-HSA antibody (concentration: 400 µg/ml) was also poured at a flow rate of 5 µl/min to immobilize for 60 minutes. HSA antigen (10 µg/ml) complementary to this anti-HSA antibody was introduced and after the reaction, a signal of about 250 RU was obtained.

| Concentration of HSA antigen (µg/ml) | 0.01 | 0.1 | 1 | 10 | 100 | 1000 |
|---|---|---|---|---|---|---|
| RU | 5 | 10 | 50 | 250 | 500 | 550 |

It was confirmed by the XPS analysis that the resulting membrane has a primary amine.

Example 13

The same apparatus and method as in Example 1 were used.

Conditions for plasma polymerization layer formation were the same as in Example 12.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 µl/min for 10 minutes and the Fab fragment of an anti-HSA antibody (concentration: 400 µg/ml) was also poured at a flow rate of 5 µl/min to immobilize for 60 minutes.

A HSA antigen (10 µg/ml) complementary to this Fab fragment of the anti-HSA antibody was introduced and after the reaction, a signal of about 275 RU was obtained.

| Concentration of HSA antigen (µg/ml) | 0.01 | 0.1 | 1 | 10 | 100 | 1000 |
|---|---|---|---|---|---|---|
| RU | 5.5 | 11 | 55 | 275 | 550 | 605 |

It was confirmed by the XPS analysis that the resulting membrane has a primary amine.

Example 14

The same apparatus and method as in Example 1 were used.

Conditions for plasma polymerization layer formation were the same as in Example 13.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 µl/min for 10 minutes and the F(ab)$_2$ fragment of an anti-HSA antibody (concentration: 400 µg/ml) was also poured at a flow rate of 5 µl/min to immobilize for 60 minutes.

A HSA antigen (10µg/ml) complementary to this F(ab)$_2$ fragment of the anti-HSA antibody was introduced and after the reaction, a signal of about 300 RU was obtained.

| Concentration of HSA antigen (µg/ml) | 0.01 | 0.1 | 1 | 10 | 100 | 1000 |
|---|---|---|---|---|---|---|
| RU | 6 | 12 | 60 | 300 | 600 | 660 |

It was confirmed by the XPS analysis that the resulting membrane has a primary amine.

Example 15

The same apparatus and method as in Example 1 were used.

Conditions for plasma polymerization layer formation were as follows:

(1) Monomer: hexadiene

Flow volume of monomer material: 1.5 sccm+Ar dilution 15 (scam)

Temperature: room temperature

Pressure: 1.6 Pa

Discharge electric power: 80 W

Discharge frequency: 13.56 MHz

Duration of discharge: 15 seconds;

(2) Monomer: ethylenediamine
Flow volume of monomer material: 1.5 sccm
Temperature: room temperature
Pressure: 1.6 Pa
Discharge electric power: 80 W
Discharge frequency: 13.56 MHz
Duration of discharge: 5 seconds.

The targeted surface was obtained by the two-step process above.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 µl/min for 10 minutes and an anti-HSA antibody (concentration: 400 µg/ml) was also poured at a flow rate of 5 µl/min to immobilize for 60 minutes. A HSA antigen (10 µg/ml) complementary to this anti-HSA antibody was introduced and after the reaction, a signal of about 250 RU was obtained.

| Concentration of HSA antigen (µg/ml) | 0.01 | 0.1 | 1 | 10 | 100 | 1000 |
|---|---|---|---|---|---|---|
| RU | 5 | 10 | 50 | 250 | 500 | 550 |

It was confirmed by the XPS analysis that the resulting membrane has a primary amine.

Example 16

The same apparatus and method as in Example 1 were used.

Conditions for plasma polymerization layer formation were as follows:
(1) Monomer: hexamethyldisiloxane
Flow volume of monomer material: 1.5 sccm+Ar dilution 15 (sccm)
Temperature: room temperature
Pressure: 1.6 Pa
Discharge electric power: 80 W
Discharge frequency: 13.56 MHz
Duration of discharge: 15 seconds;
(2) Monomer: ethylenediamine
Flow volume of monomer material: 1.5 sccm
Temperature: room temperature
Pressure: 1.6 Pa
Discharge electric power: 80 W
Discharge frequency: 13.56 MHz
Duration of discharge: 5 seconds.

The targeted surface was obtained by the two-step process above.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 µl/min for 10 minutes and an anti-HSA antibody (concentration: 400 µg/ml) was also poured at a flow rate of 5 µl/min to immobilize for 60 minutes. A HSA antigen (10 µg/ml) complementary to this anti-HSA antibody was introduced and after the reaction, a signal of about 225RU was obtained.

| Concentration of HSA antigen (µg/ml) | 0.01 | 0.1 | 1 | 10 | 100 | 1000 |
|---|---|---|---|---|---|---|
| RU | 4.5 | 9 | 45 | 225 | 450 | 495 |

It was confirmed by the XPS analysis that the resulting membrane has a primary amine.

Example 17

The same apparatus and method as in Example 1 were used.

Conditions for plasma polymerization layer formation were the same as in Example 2 except that propylamine was used as a monomer material.

Under the conditions described above, a plasma polymerization layer was formed. The sensor chip was mounted on the cartridge block of the surface plasmon resonance biosensor, 5% glutaraldehyde was poured through a flow route into the measuring cell at a flow rate of 5 µl/min for 10 minutes and avidin (concentration: 20 µg/ml) was also poured at a flow rate of 5 µl/min to immobilize for 60 minutes. 10 µM biotin-labeled probe RNA was poured at a flow rate of 1 µl/min to immobilize the probe RNA for 10 minutes. DNA (7.5×10M) having a DNA sequence complementary to this probe RNA was introduced and after the reaction, a signal of about 400 RU was obtained.

| Concentration of Complementary DNA (µM) | 0.00075 | 0.0075 | 0.075 | 0.75 | 7.5 | 75 |
|---|---|---|---|---|---|---|
| RU | 8 | 20 | 80 | 400 | 800 | 880 |

It was confirmed by the XPS analysis that the resulting membrane has a primary amine.

Example 18

The same apparatus and method as in Example 1 were used.

Conditions for plasma polymerization layer formation were as follows:
(1) Monomer: propargyl alcohol
Flow volume of monomer material: 1.5 sccm
Temperature: room temperature
Pressure: 1.6 Pa
Discharge electric power: 20 W
30 Discharge frequency: 13.56 MHz
Duration of discharge: 15 seconds;
(2) Monomer: oxygen (plasma treatment)
Flow volume of monomer material: 1.5 sccm
Temperature: room temperature
Pressure: 1.6 Pa Discharge electric power: 20 W Discharge frequency: 13.56 MHz Duration of discharge: 5 seconds.

The targeted surface was obtained by the two-step process above.

Under the conditions described above, a plasma polymerization layer was formed. The sensor chip was mounted on the cartridge block of the surface plasmon resonance biosensor, a 0.5 M carbodiimide solution was poured through a flow route into the measuring cell at a flow rate of 5 μl/min for 10 minutes and an anti-HSA antibody (concentration: 400 μg/ml) was also poured at a flow rate of 5 μg/min to immobilize for 60 minutes. A HSA antigen (10 μg/ml) complementary to this anti-HSA antibody was introduced and after the reaction, a signal of about 250 RU was obtained.

| Concentration of HSA antigen (μg/ml) | 0.01 | 0.1 | 1 | 10 | 100 | 1000 |
|---|---|---|---|---|---|---|
| RU | 5 | 10 | 50 | 250 | 500 | 550 |

It was confirmed by the XPS analysis that the resulting membrane has a carboxyl group.

Example 19

The same apparatus and method as in Example 1 were used.

Conditions for plasma polymerization layer formation were the same as in Example 2 except that propagylamine was used as a monomer material.

Under the conditions described above, a plasma polymerization layer was formed. The sensor chip was mounted on the cartridge block of the surface plasmon resonance biosensor, 0.5 M carbodiimide was poured through a flow route into the measuring cell at a flow rate of 5 μl/min for 10 minutes and behenic acid (concentration: 400 μg/ml) was also poured at a flow rate of 5 μl/min to immobilize for 60 minutes. Skatole (10 μg/ml) complementary to this behenic acid was introduced and after the reaction, a signal of about 225 RU was obtained.

| Concentration of skatole (μg/ml) | 0.01 | 0.1 | 1 | 10 | 100 | 1000 |
|---|---|---|---|---|---|---|
| RU | 4.5 | 9 | 45 | 225 | 450 | 495 |

It was confirmed by the XPS analysis that the resulting membrane has a primary amine.

Example 20

Example 20 shows a formation of hydrophobic bond.

A layer comprising chrome and gold was formed on a transparent substrate (glass plate) by sputtering. A plasma polymerization layer in which trifluoroethylene was used as a monomer was then formed on the resulting metal layer under the following conditions:

Flow volume: 1.5 sccm

Temperature: room temperature

Pressure: 5 Pa

Discharge electric power: 50 W

Discharge frequency: 13.56 MHz

Duration of discharge: 30 seconds.

The plasma polymerization layer obtained under the conditions described above was hydrophobic. An anti-HSA antibody (concentration: 100 μg/ml) was allowed to flow at a flow rate of 5 μl/min for 60 minutes to immobilize the antibody via hydrophobic bond. HSA at a specified concentration was further reacted with this antibody-immobilized plasma polymerization layer. The following results were obtained.

| Concentration of HSA antigen (μg/ml) | 0.01 | 0.1 | 1 | 10 | 100 | 1000 |
|---|---|---|---|---|---|---|
| RU | 3 | 6 | 30 | 150 | 300 | 330 |

Example 21

Example 21 shows an inclusion of an antibody by plasma polymerization.

A layer comprising chrome and gold was formed on a transparent substrate (glass plate) by sputtering. A plasma polymerization layer in which propargyl alcohol was used as a monomer was then formed on the resulting metal layer under the following conditions:

Flow volume: 1.5 sccm

Temperature: room temperature

Pressure: 1.6 Pa

Discharge electric power: 20 W

Discharge frequency: 13.56 MHz

Duration of discharge: 15 seconds.

The plasma polymerization layer obtained under the conditions described above was highly hydrophilic. An antibody solution (concentration: 100 μg/ml) was spread evenly on this propargyl alcohol plasma polymerization layer and after drying, plasma treatment was further carried out on this surface under the following conditions:

Flow volume: 1.5 sccm

Temperature: room temperature

Pressure: 1.6 Pa

Discharge electric power: 20 W

Discharge frequency: 13.56 MHz

Duration of discharge: 8 seconds.

HSA at a specified concentration was reacted with the membrane in which the antibody was thus integrated and immobilized by plasma treatment. The following results were obtained, from which a calibration curve could be drawn.

| Concentration of HSA antigen (μg/ml) | 0.01 | 0.1 | 1 | 10 | 100 | 1000 |
|---|---|---|---|---|---|---|
| RU | 5 | 10 | 50 | 250 | 500 | 550 |

*Flow rate for HSA: 5 μl/min.

What is claimed is:

1. A measuring chip for a surface plasmon resonance sensor comprising:
   a thin gold film,
   one or more plasma polymerization layers formed on said thin gold film and
   a physiologically active substance immobilized on one or more of said plasma polymerization layers,
   wherein said plasma polymerization layer is formed from a monomeric compound having —C≡CCH$_2$OH.

2. The measuring chip of claim 1 for a sensor wherein said physiologically active substance is selected from the group consisting of a: non-immune protein; immunoglobulin-binding protein: sugar-binding protein; sugar-recognizing sugar chain; fatty acid or fatty acid ester; polypeptide or oligopeptide having ligand binding activity; immune protein; enzyme; and a nucleic acid.

3. A measuring chip for a surface plasmon resonance sensor according to claim 2, wherein said nucleic acid is DNA, RNA or PNA.

4. A measuring chip according to claim 1, which further comprises an optically transparent substrate on which said thin gold film is formed.

5. A measuring chip according to claim 1, wherein said plasma polymerization layer consists of two or more layers.

6. A measuring chip according to claim 1, wherein said monomer material of plasma polymerization layer is a mixture of two or more monomers.

7. A measuring chip according to claim 2, wherein said nucleic acid is immobilized on said plasma polymerization layer through a cross-linking reagent or a condensation reagent.

8. A measuring chip according to claim 7, wherein said cross-linking reagent is one or more compounds selected from the group consisting of glutaraldehyde, periodic acid, N-succinimidyl-2-maleimidoacetic acid, N-succinimidyl-4-maleimidobutyric acid, -succinimidyl-6-maleimidohexanic acid, N-succinimidyl-4-maleimidomethylcyclohexan-1-carboxylic acid, N-sulfosuccinimidyl-4-maleimidomethylcyclohexane-1-carboxylic acid, N-succinimidyl-4-maleimidomethylbanzoic acid, N-succinimidyl-3-maleimidobenzoic acid, N-sulfosuccinimidyl-3-maleimidobenzoic acid, N-succinimidyl-4-maleimidophenyl-4-butyric acid, N-sulfosuccinimidyl-4-maleimidophenyl-4-butyric acid, N,N'-oxydimethylene-dimaleimide, N,N'-o-phenylene-dimaleimide, N,N'-m-phenylene-dimaleimide, N,N'-p-phenylene-dimaleimide, N,N'-hexamethylene-dimaleimide, N-succinimidylmaleimidocarboxylic acid, N-succinimidyl-S-acetylmercaptoacetic acid, N-succinimidyl-3-(2-pyridyldithio)propionate, S-acetylmercaptosuccinic anhydride, methyl-3-(4'-dithiopyridyl)propionimidate, methyl-4-mercaptobutylimidate, methyl-3-mercaptopropionimidate, iminothiolene, o-carboxymethyl-hydroxylamine, azodiphenylpilmaleido, bis(sulfosuccinimidyl)sperate, 4,4'-diisothiocyano-2,2'-disulfonic acid stilbene, 4,4'-difluoro-3,3'-dinitrodiphenylsulfon, 1,5-difluoro-2,4-dinitrobenzene, p-phenylenediisothiocyanate, dimethyladipimidate, dimethylpimelimidate, dimethylsuberimidate, p-azidophenacylbromide, p-azidophenylglyoxal, N-hydroxysuccinimidyl-4-azidobenzoate, 4-fluoro-3-nitrophenylazide, methyl-4-azidobenzoimidate, N-5-azido-2-nitrobenzoyloxysuccinimide, N-succinimidyl-6-(4'-azido-2'-nitrophenylamino)hexanoate, 1,4-benzoquinone, N-succinimidyl-3-(2'-pyridyldithio)propionate, N-(4-maleimidobutyloxy)sulfosuccinimide sodium salt, N-(6-maleimidocaproyloxy)sulfosuccinimide sodium salt, N-(8-maleimidocaproyloxy)sulfosuccinimide sodium salt, N-(11-maleimidoundecanoyloxy)sulfosuccinimide sodium salt, N-[2-(1-piperazinyl)ethyl]maleimide bichloric acid, bisdiazobenzidine, hexamethylenediisocyanate, toluenediisocyanate, hexamethylenediisothiocyanate, N,N'-ethylenebismaleinimide, N,N'-polymethylenebisiodoacetamide, 2,4-dinitrobenzenesulfonate sodium salt, and diazo compounds; or said condensation reagent is one or more compounds selected from the group consisting of carbodiimide derivatives represented by RN=C=NR (or R'), N-hydroxysuccinimide, tri-n-butylamine, butyl chloroformate, and isobutyl isocyanide.

9. A measuring chip for a surface plasmon resonance sensor according to claim 1, which further comprises an additional plasma polymerization layer or plasma-treated layer formed on said plasma polymerization layer.

10. A method for producing a measuring chip for a surface plasmon resonance sensor according to claim 1 comprising:
   forming a thin gold film on an optically transparent substrate,
   forming one or more plasma polymerization layers on said thin gold film, and
   then immobilizing a physiologically active substance on the surface of said plasma polymerization layer,
   wherein at least one of said plasma polymerization layer(s) is formed from a monomeric compound having—C≡CCH$_2$OH.

11. A method according to claim 10, wherein the plasma polymerization layer is formed by a plasma-treatment using a monomer material.

12. A method for producing a measuring chip for a surface plasmon resonance sensor according to claim 1 comprising:
   forming a thin gold film on an optically transparent substrate,
   forming one or more plasma polymerization layers on said thin gold film by a plasma-treatment using a monomer material comprising nitrogen, sulfur, oxygen, a halogen, an organic compound, an organic metal compound or an organic silicon compound, and then
   immobilizing a physiologically active substance on the surface of said plasma polymerization layer,
   wherein at least one of said plasma polymerization layer(s) is formed from a monomeric compound having—C≡CCH$_2$OH.

13. A measuring cell for a surface plasmon resonance sensor comprising a measuring chip according to claim 1.

14. A measuring cell according to claim 13, wherein said chip is optically analyzed.

15. A surface plasmon resonance biosensor comprising a measuring chip according to claim 1.

16. A surface plasmon resonance biosensor comprising a measuring cell according to claim 13 or 14.

* * * * *